United States Patent
Weidhaas

(10) Patent No.: US 12,297,509 B2
(45) Date of Patent: May 13, 2025

(54) BIOMARKERS FOR PREDICTING TUMOR RESPONSE TO AND TOXICITY OF IMMUNOTHERAPY

(71) Applicant: Mira Dx, Inc., Los Angeles, CA (US)

(72) Inventor: Joanne Weidhaas, Los Angeles, CA (US)

(73) Assignee: MIRA DX, INC., Los Angeles, CA (US)

(*) Notice: Subject to any disclaimer, the term of this patent is extended or adjusted under 35 U.S.C. 154(b) by 0 days.

(21) Appl. No.: 18/163,723

(22) Filed: Feb. 2, 2023

(65) Prior Publication Data
US 2024/0132966 A1  Apr. 25, 2024

Related U.S. Application Data

(63) Continuation of application No. 16/622,778, filed as application No. PCT/US2018/037866 on Jun. 15, 2018, now Pat. No. 11,578,371.

(60) Provisional application No. 62/520,459, filed on Jun. 15, 2017.

(51) Int. Cl.
| | |
|---|---|
| *C12Q 1/6886* | (2018.01) |
| *A61K 39/00* | (2006.01) |
| *A61N 5/10* | (2006.01) |
| *C07K 16/28* | (2006.01) |

(52) U.S. Cl.
CPC ............ *C12Q 1/6886* (2013.01); *A61K 39/00* (2013.01); *A61N 5/1001* (2013.01); *A61N 5/1077* (2013.01); *C07K 16/2818* (2013.01); *C07K 16/2827* (2013.01); *A61N 2005/1098* (2013.01); *C12Q 2600/106* (2013.01); *C12Q 2600/112* (2013.01); *C12Q 2600/156* (2013.01); *C12Q 2600/178* (2013.01)

(58) Field of Classification Search
CPC .................................................. C12Q 1/6886
USPC ...................................................... 424/172.1
See application file for complete search history.

(56) References Cited

U.S. PATENT DOCUMENTS

| | | | |
|---|---|---|---|
| 2003/0087818 A1* | 5/2003 | Jiang ...................... | C07K 14/47 514/19.3 |
| 2006/0253263 A1 | 11/2006 | Meshkin | |
| 2008/0081076 A1 | 4/2008 | Lisonbee et al. | |
| 2013/0052160 A1 | 2/2013 | Zitvogel et al. | |
| 2015/0232836 A1 | 8/2015 | Krieg et al. | |
| 2017/0174774 A1* | 6/2017 | Coric ................. | A61K 39/0008 |

FOREIGN PATENT DOCUMENTS

| | | |
|---|---|---|
| WO | 2014/193937 A1 | 12/2014 |
| WO | 2015/184061 A2 | 12/2015 |
| WO | 2017/189906 A1 | 11/2017 |

OTHER PUBLICATIONS

Raedler et al (American Health & Drug Benefits, 2015, 8: 180-183).*
Gast et al (PLoS ONE, 2011, 6(9)(e24370):1-7).*
Graff et al (Oncotarget, 2016, 7(33): 52810-52817).*
Weng et al (PLoS ONE, 2014, 9(10)(e110569):1-12).*
Garon et al (NEJM, 2015, 372(21): 2018-2028).*
He et al (Cancer Genetics, 2015, 208: 310-318).*
Matuschek et al (Radiation Oncology, 2015, 10(71): 1-9).*
Bagratuni et al (Blood, 2013, 122(21): 1861).*
Kurt et al (Inflammation, 2016, 39(1): 166-171).*
Kasamatsu et al (Hematol Oncol, 2016, 1-8).*
Kanchi et al. "*Homo sapiens* FOSMID clone A BC9-44004300J20 from chromosome 9, complete sequence" National Center for Biotechnology Information. Genbank Entry [online]. Jul. 29, 2008 [retrieved Oct. 3, 2018]. Retrieved from the internet: <URL: <https://www.ncbi.nlm.nih.gov/nucleotide/AC207594>>; pp. 1-9.
Clark, G. "Human DNA sequence from clone RP11-574F11 on chromosome 9 complete sequence" National Center for Biotechnology Information. Genbank Entry [online]. Dec. 13, 2012 [retrieved Oct. 3, 2018]. Retrieved from the internet: <URL: <https://www.ncbi.nlm.nih.gov/nucleotide/AL162253.17>>; pp. 1-32.
Van Allen et al. (2015) "Long-term Benefit of PD-L1 Blockade in Lung Cancer Associated with JAK3 Activation," Cancer Immunology Research 3(8):855-863.
Dudley et al. (2016) "Microsatellite Instability as a Biomarker for PD-1 Blockade," Clinical Cancer Research 22 (4):813-820.
Tan et al. (2017) "Immune Checkpoints in Gliomas," Current Oncology Reports, Current Science 19(4):1-11.
Chen et al. (2013) "Oncology Meets Immunology: The Cancer-Immunity Cycle," Immunity 39(1):1-10.
Rizvi et al. (2015) "Mutational landscape determines sensitivity to PD-1 blockade in non-small cell lung cancer," Science, 348(6230):124-128.
Tockman et al. "Considerations in bringing a cancer biomarker to clinical application" Cancer Res., May 1, 1992;52(9 Suppl); pp. 2711s-2718s.
Ferrandina et al. "Cyclo-oxygenase-2 (Cox-2) expression and resistance to platinum versus platinum/paclitaxel containing chemotherapy in advanced ovarian cancer" BMC Cancer 2006, 6:182 doi:10.I 186/1471-2407-6-182; pp. 1-7.
Topalian et al. "Survival, Durable Tumor Remission, and Long-Term Safety in Patients With Advanced Melanoma Receiving Nivolumab" J Clin Oncol. Apr. 1, 2014; 32(10): pp. 1020-1030.
Wolchok et al. "Nivolumab Plus Ipilimumab in Advanced Melanoma" NEJM, 2013, 369(2): pp. 122-133.
Watahiki et al. "Libraries enriched for alternatively spliced exons reveal splicing patterns in melanocytes and melanomas" Nat Methods 1, 2004, 1 (3); pp. 233-239.
Abdel-Wahab et al. Adverse Events Associated with Immune Checkpoint Blockade in Patients with Cancer: A systematic Review of Case Reports, PLOS One, vol. 11, No. 7, Jul. 29, 2016 (Jul. 29, 2016), p. e0160221, XP93124905, US ISSN: 1932-6203, DOI: 10.1371/journal.pone.0160221.

* cited by examiner

*Primary Examiner* — Sean E Aeder
(74) *Attorney, Agent, or Firm* — Goodwin Procter LLP

(57) ABSTRACT

The invention is directed to biomarkers for predicting a patient's response, both therapeutic and toxic, to immunotherapy.

15 Claims, 7 Drawing Sheets

Specification includes a Sequence Listing.

| SEQ ID NO: | Gene Name | NCBI ID NO. (if applicable) | SEQUENCE |
|---|---|---|---|
| 1 | CD44 | rs11821102 | AACTTATGTGCTTAACAGGCAATGCTTCTCAGACCACAAAGCAGAAAGAAGAAGAAA AGCTCCTGACTAAATCAGGGCTGGGCTTAGACAGAGTTGATCT[A]TAGAATATCTT TAAAGGAGAGATGTCAACTTTCTGCACTATTCCCAGCCCTCTGCTCCTCCCTGTCTAC CCTCTCCCCCTCCCCTCTCTCCCCTCCACTTCACC |
| 17 | CD44 | Wild-type | AACTTATGTGCTTAACAGGCAATGCTTCTCAGACCACAAAGCAGAAAGAAGAAGAAA AGCTCCTGACTAAATCAGGGCTGGGCTTAGACAGAGTTGATCT[G]TAGAATATCTT TAAAGGAGAGATGTCAACTTTCTGCACTATTCCCAGCCCTCTGCTCCTCCCTGTCTAC CCTCTCCCCCTCCCCTCTCTCCCCTCCACTTCACC |
| 2 | CD274 | rs4742098 | CATAGGCAGAGATGATACCTAATTCTGCATTGATTGTCACTTTTTGTACCTGCATT AATTTAATAAAATATTCTTATTTGTTAATAAAATGTTCAGTTAACATCCCAGTGGAGAAAGT TCTTGTTTATTTGTGTTTAATAAAATGTCAGTTAACACC[G]GCATGTCCATT TACTTGGAATATTTGCAGCCTTGTCCTAGTT |
| 18 | CD274 | Wild-type | CATAGGCAGAGATGATACCTAATTCTGCATTGATTGTCACTTTTTGTACCTGCATT AATTTAATAAAATATTCTTATTTGTTAATAAAATGTTCAGTTAACATCCCAGTGGAGAAAGT TCTTGTTTATTTGTGTTTAATAAAATGTCAGTTAACACC[A]GCATGTCCATT TACTTGGAATATTTGCAGCCTTGTCCTAGTT |
| 3 | EXO1 | rs4150021 | CAAGAGAATCTGATCAATTGAAGTCCCTGTTTGGGAATGAGGCACTTATCAGCATG AAGAATTTTTCTCATTCTGTGCCATTTAAAAAATAGAATACA[-]TTTGTATATTA ACTTTATAATTGGGTTGTGGTTTTTTGCTCAGCTTTTTATATTTTTATAAGAAGCT AAATAGAAGAATAATTGTATCTCTGACAGGTT |
| 19 | EXO1 | Wild-type | CAAGAGAATCTGATCAATTGAAGTCCCTGTTTGGGAATGAGGCACTTATCAGCATG AAGAATTTTTCTCATTCTGTGCCATTTAAAAAATAGAATACA[T]TTTGTATATTA ACTTTATAATTGGGTTGTGGTTTTTTGCTCAGCTTTTTATATTTTTATAAGAAGCT AAATAGAAGAATAATTGTATCTCTGACAGGTT |
| 4 | IL8 | rs4073 | AAGAAAATCATCCATGATGATAAAGTTATCTAGAGAAATAAAAAGCATACA[A]TTGATAATTCA CATGGTACTATGATAAAGTTATCTAGAGAAATAAAAAGCATACA[A]TTGATAATTCA CCAAATTGTGGAGCTTCAGTATTTAAATGTATATTAAAATTAATTATTTTAAGA TCAAAGAAAACTTTCGTCATACTCCGTATTTG |

FIGURE 1

| SEQ ID NO: | Gene Name | NCBI ID NO. (if applicable) | SEQUENCE |
|---|---|---|---|
| 20 | IL8 | Wild-type | AAGAAAATCATCCATGATCTTGTTCTAACACCTGCCACTCTAGTACTATATCGTCA CATGGTACTATGATAAAGTTATCTAGAGAAATAAAAAAGCATACA[T]TTGATAATTCA CCAAATTGTGGAGCTTCAGTATTTAAAGTATATTAAAATTAAATTATTTTAAAGA TCAAAGAAAACTTTCGTCATACTCCGTATTTG |
| 5 | IL10 | rs3024496 | AAAAATTATAATATATTGGGCTTCTTCTAAATCGTTCACAGAGAAGCTCAGTAAATAA ATAGAAATGGGGGTTGAGGTATCAGAGAGTAATAAATATTCTAT[G]AGAGAGTACA ATAAGGTTTCTCAAGGGGCTGGGTCAGCTATCCCAGAGCCCCAGATCCGATTTTGGA GACCTCTAATTTATGTCCTAGAGTCTATAGAG |
| 21 | IL10 | Wild-type | AAAAATTATAATATATTGGGCTTCTTCTAAATCGTTCACAGAGAAGCTCAGTAAATAA ATAGAAATGGGGGTTGAGGTATCAGAGAGTAATAAATATTCTAT[A]AGAGAGTACA ATAAGGTTTCTCAAGGGGCTGGGTCAGCTATCCCAGAGCCCCAGATCCGATTTTGGA GACCTCTAATTTATGTCCTAGAGTCTATAGAG |
| 6 | IL10RB | rs2834167 | TATTTCATAGCATTGGAATGTACCACCTCCCGAAAATGTCAGAATGAATTCTGT TAATTTCAAGAACATTCTACAGTGGAGTCACCTGCTTTTGCC[G]AAGGAACCTG ACTTTCACACGTCAGTACCTAAGGTGGGTCTGGCCTCACTATTGGCAGGAACGCACC GGAGGAGCCAGCCCTGGGCTGGTCACTGGGTT |
| 22 | IL10RB | Wild-type | TATTTCATAGCATTGGAATGTACCACCTCCCGAAAATGTCAGAATGAATTCTGT TAATTTCAAGAACATTCTACAGTGGAGTCACCTGCTTTTGCC[A]AAGGAACCTG ACTTTCACACGTCAGTACCTAAGGTGGGTCTGGCCTCACTATTGGCAGGAACGCACC GGAGGAGCCAGCCCTGGGCTGGTCACTGGGTT |
| 7 | IL18R1 | rs11465660 | TTGGCATAAGGCAGCATGGTTGCTACTTCTGTGCCTCTGGAAGATGGGCTGTGCAGCCCATCCTGA GCTCCAGTCCTGAGTTTGCTACTTCTGTGCCCTCTGGAA[A]CTTATCCAACC TCTTGGTGCTTCAGTTTCCTCATCTGTGAATTAGAATTATAATTGCACCTAC CTCCCAGGGGTAACTAAATGAATAAATATAT |
| 23 | IL18R1 | Wild-type | TTGGCATAAGGCAGCATGGTGTGCAGTTAAGAGATGGGCTGTGCAGCCCATCCTGA GCTCCAGTCCTGAGTTTGCTACTTCTGTGCCCTCTGGAA[C]CTTATCCAACC TCTTGGTGCTTCAGTTTCCTCATCTGTGAATTAGAATTATAATTGCACCTAC CTCCCAGGGGTAACTAAATGAATAAATATAAT |

FIGURE 1 (continued)

| SEQ ID NO: | Gene Name | NCBI ID NO. (if applicable) | SEQUENCE |
|---|---|---|---|
| 8 | miR99a promoter | variant | CAAGGGGGTGGAGGAGAGCGGGAAGGAGGGGTGTCAGCTCAACTGTAAAAGCT GCACAGATTTTTTCTTTCTTCGCATTCGCATAGCTAAAAAGAATGCTAATTAAGATCCCTGTTTC ATGCCCTGTCTCATTTCGCATAGCTAAAAAGAATGCTAATTAAGATCCCTTGTCTT AACCTGAAAAATAATGACTCGGCTGTAATTAG |
| 24 | miR99a promoter | Wild-type | CAAGGGGGTGGAGGAGAGCGGGAAGGAGGGGTGTCAGCTCAACTGTAAAAGCT GCACAGATTTTTTCTTTCTTCGCATTCGCATAGCTAAAAAGAATGCTAATTAAGATCCCTGTTTC ATGCCCTGTCTCATTTCGCATAGCTAAAAAGAATGCTAATTAAGATCCCTTGTCTT AACCTGAAAAATAATGACTCGGCTGTAATTAG |
| 9 | RAD23A | rs8240 | GAGGGAAGCTGGAGCCTGGAACTTTGATCCTCCATTGGAGTGGCCCAAATCTTTCCA TCTAGGGCAAGTCCTGAAAGGCCCAAGCCCCCTCCCCAGTCT[A]GCCTTGGCCTC CAGCCCTGGAGAAGGGCTAACATCAGCTCATTGTCAAGGCCACCCCCAGAACA GAACCGTGTCTCTGATAAAGGTTTTGAAGTGA |
| 25 | RAD23A | Wild-type | GAGGGAAGCTGGAGCCTGGAACTTTGATCCTCCATTGGAGTGGCCCAAATCTTTCCA TCTAGGGCAAGTCCTGAAAGGCCCAAGCCCCCTCCCCAGTCT[G]GCCTTGGCCTC CAGCCCTGGAGAAGGGCTAACATCAGCTCATTGTCAAGGCCACCCCCAGAACA GAACCGTGTCTCTGATAAAGGTTTTGAAGTGA |
| 10 | STAT3 | rs3744483 | CGTCGCTGCTGGGGCCCCATAGTGTCGAGACATCATGTCCAACCTGTAACTCTCTCCCCCTCTT CTTCCATGAGGTCCTGAGACCAAGACATTCCTAAAACAAACAGGA[C]GAGGGACCTTT AGACACGCAAGGAGACATGCCTCTAGCAGGATCAGGGGACTGGGGTCGGGAGGGTG GGGCAGGAAGGAAGCCAGAATCAGAAGTATCC |
| 26 | STAT3 | Wild-type | CGTCGCTGCTGGGGCCCCATAGTGTCGAGACATCATGTCCAACCTGTAACTCTCTCCCCCTCTT CTTCCATGAGGTCCTGAGACCAAGACATTCCTAAAACAAACAGGA[T]GAGGGACCTTT AGACACGCAAGGAGACATGCCTCTAGCAGGATCAGGGGACTGGGGTCGGGAGGGTG GGGCAGGAAGGAAGCCAGAATCAGAAGTATCC |
| 11 | EREG | rs1460008 | AAGTTTGAAGAGCCATTTGTAAACGTTTTATTAAAGATGCTATGGAACATAAA GTGTATTGCATGCAATTGAAGTAACTTATTTGACTATGAAT[G]TTATCGGATTA CTGAATTGTATCAATTTGTGTTCAATATCAGCTTTGATAATTGTGTACCTTAA GATATATTGAAGGAGAGAAATAGATAATTTACAAG |

FIGURE 1 (continued)

| SEQ ID NO: | Gene Name | NCBI ID NO. (if applicable) | SEQUENCE |
|---|---|---|---|
| 27 | EREG | Wild-type | AAGTTTGAAGAGCCATTTGGTAAACGGTTTTATTAAAGATGCTATGGAACATAAA GTTGTATTGCATGCAATTGAAGTAACTTATTTGACTATGAAT[A]TTATCGGATTA CTGAATTGTATCAATTTGTTTGTGTTCAATATCAGCTTTGATAATTGTGTACCTTAA GATATTGAAGGAGAAAATAGATAATTTACAAG |
| 12 | FCGR2A | rs10919033 | CCATGTCAACAGTAATAACTAAAGAGTAACGTTATGCCATGTGGTCATACTCTCAGC TTGCTGAGTGGATGACAAAAAGAGGGGAATTGTTAAAGGAAAA[C]TTAAATGGAGA CTGGAAAAATCCTGAGCAAACAAAACAACCACCTGGCCCTTAGAAATAGCTTTAACTTTG CTTAAACTACAAACACAAGCAAAACTTCACGG |
| 28 | FCGR2A | Wild-type | CCATGTCAACAGTAATAACTAAAGAGTAACGTTATGCCATGTGGTCATACTCTCAGC TTGCTGAGTGGATGACAAAAAGAGGGGAATTGTTAAAGGAAAA[T]TTAAATGGAGA CTGGAAAAATCCTGAGCAAACAAAACAACCACCTGGCCCTTAGAAATAGCTTTAACTTTG CTTAAACTACAAACACAAGCAAAACTTCACGG |
| 13 | FCGR2A | rs1801274 | AGGCTTGGATGAGAACAGCGTGTAGCCTATGTTTCCTGTGCAGTGGTAATCACCACT GTGACTGTGGTTTGCTTGTGGGATGGAGAAGGTGGGATCCAAA[C]GGGAGAATTTC TGGGATTTTCCATTCTGGAAGAATGTGACCTTGACCAGAGGCTTGTCCTTCCAGCTG TGGCACCTCAGCATGATGGTTTCTCCCTCCTG |
| 29 | FCGR2A | Wild-type | AGGCTTGGATGAGAACAGCGTGTAGCCTATGTTTCCTGTGCAGTGGTAATCACCACT GTGACTGTGGTTTGCTTGTGGGATGGAGAAGGTGGGATCCAAA[T]GGGAGAATTTC TGGGATTTTCCATTCTGGAAGAATGTGACCTTGACCAGAGGCTTGTCCTTCCAGCTG TGGCACCTCAGCATGATGGTTTCTCCCTCCTG |
| 14 | KRAS | rs61764370 | AGGCGTGTGCCACTACACTCAACTAATTTTTGTATTTTTAGGAGAGACGGGGTTTCA CCCTGTTGGCCAGGCTGGTCTCGAACTCCTGACCTCAAGTGAT[G]CACCCACCTTG GCCTCATAAACCTGTTTTGCAGAACTCATTATTCAGCAAATATTATTGAGTGCCT ACCAGATGCCAGTGCCACACCAAGGCACTGGG |
| 30 | KRAS | Wild-type | AGGCGTGTGCCACTACACTCAACTAATTTTTGTATTTTTAGGAGAGACGGGGTTTCA CCCTGTTGGCCAGGCTGGTCTCGAACTCCTGACCTCAAGTGAT[T]CACCCACCTTG GCCTCATAAACCTGTTTTGCAGAACTCATTATTCAGCAAATATTATTGAGTGCCT ACCAGATGCCAGTGCCACACCAAGGCACTGGG |

FIGURE 1 (continued)

| SEQ ID NO: | Gene Name | NCBI ID NO. (if applicable) | SEQUENCE |
|---|---|---|---|
| 15 | RAC1 | rs9374 | TCTAAATGTAAGAGTTCAGACTCACATTCTATTAAAATTTAGCCCTAAAATGACAAG CCTTCTTAAAGCCTTATTTTCAAAAGCGCCCCCATTCTT[A]TTCAGATTAAG AGTTGCCAAAATACCTTCTGAACTACACTGCATTGTTGTGCCGAGAACACCGAGCAC TGAACTTTGCAAAGACCTTCGTCTTTGAGAAG |
| 31 | RAC1 | Wild-type | TCTAAATGTAAGAGTTCAGACTCACATTCTATTAAAATTTAGCCCTAAAATGACAAG CCTTCTTAAAGCCTTATTTTCAAAAGCGCCCCCATTCTT[G]TTCAGATTAAG AGTTGCCAAAATACCTTCTGAACTACACTGCATTGTTGTGCCGAGAACACCGAGCAC TGAACTTTGCAAAGACCTTCGTCTTTGAGAAG |
| 16 | TRL4 | rs4986790 | GAAGGAAACTTGGAAAAGTTTGACAAATCTGCTCTAGAGGGCCTGTGCAATTTGACC ATTGAAGAATTCCGATTAGCATACTTAGACTACTACCTCGATG[G]TATTATTGACT TATTTAATTGTTTGACAAATGTTTCTTCATTTTCCCTGGTGAGTGTGACTATTGAAA GGGTAAAAGACTTTTCTTATAATTTCGGATGG |
| 32 | TRL4 | Wild-type | GAAGGAAACTTGGAAAAGTTTGACAAATCTGCTCTAGAGGGCCTGTGCAATTTGACC ATTGAAGAATTCCGATTAGCATACTTAGACTACTACCTCGATG[A]TATTATTGACT TATTTAATTGTTTGACAAATGTTTCTTCATTTTCCCTGGTGAGTGTGACTATTGAAA GGGTAAAAGACTTTTCTTATAATTTCGGATGG |
| 33 | MSH2 | rs2303428 | AAACCTACGCGATTAATCATCAGTGTACAGTTTAGGACTAACAATCCATTATTAGT AGCAGAGAAGAAGTTTAAAATCTTGCTTTCTGATATAATTGTT[C]TGTAGGCCCCA ATATGGGAGGTAAATCAACATATATTCGACAAACTGGGGTGATAGTACTCATGGCCC AAATTGGGTGTTTTGTGCCATGTGAGTCAGCA |
| 34 | MSH2 | rs2303428 | AAACCTACGCGATTAATCATCAGTGTACAGTTTAGGACTAACAATCCATTATTAGT AGCAGAGAAGAAGTTTAAAATCTTGCTTTCTGATATAATTGTT[T]TGTAGGCCCCA ATATGGGAGGTAAATCAACATATATTCGACAAACTGGGGTGATAGTACTCATGGCCC AAATTGGGTGTTTTGTGCCATGTGAGTCAGCA |

FIGURE 1 (continued)

BIOMARKERS FOR PREDICTING TUMOR RESPONSE TO AND TOXICITY OF IMMUNOTHERAPY

CROSS-REFERENCE TO RELATED APPLICATIONS

This application is a continuation of U.S. patent application Ser. No. 16/622,778, allowed, which is a U.S. national stage application, filed under 35 U.S.C. § 371, of International Application No. PCT/US2018/037866, filed on Jun. 15, 2018, which claims priority to and the benefit of U.S. Application Ser. No. 62/520,459, filed on Jun. 15, 2017, the entire contents of each of which are herewith incorporated by reference in their entirety for all purposes.

SEQUENCE LISTING

The instant application contains a Sequence Listing which has been submitted electronically in XML format and is hereby incorporated by reference in its entirety. Said XML copy, created on Feb. 1, 2023, is named MIR-003C1_SL.xml and is 36,780 bytes in size.

The invention is directed to methods of using biomarkers present in a cancer patient's germline genome to predict the cancer patient's response to an immune modulating agent.

FIELD OF THE INVENTION

Background

Most cancer drugs are effective in some patients, but not in others. This results, at least in part, from genetic variation among patients. Variable patient response is particularly pronounced with respect to immunotherapy. Therefore, the full potential of immunotherapies for treating cancer cannot be realized without suitable tests for determining which patients will benefit from which drugs.

Many patients experience a toxic response to anti-cancer immunotherapies, resulting in discontinuance of therapy; however, it is difficult to predict whether or not a patient will have a toxic response to a therapy before administration.

According to the National Institutes of Health (NIH), the term "biomarker" is defined as "a characteristic that is objectively measured and evaluated as an indicator of normal biologic or pathogenic processes or pharmacological response to a therapeutic intervention" (Biomarkers Definitions Working Group, 2001, Clin. Pharmacol. Ther. 69:89-95)

The development of improved diagnostics based on the discovery of biomarkers has the potential to accelerate new drug development by identifying, in advance, those patients most likely to show a clinical response or a toxic response to a given drug. This would significantly reduce the size, length and cost of clinical trials. Technologies such as genomics, proteomics, and molecular imaging currently enable rapid, sensitive and reliable detection of specific gene mutations, expression levels of particular genes, and other molecular biomarkers. However, the clinical utilization of cancer biomarkers to predict response or toxicity remains largely unrealized because few cancer biomarkers have been discovered. For example, a recent review article states:

> There is a critical need for expedited development of biomarkers and their use to improve diagnosis and treatment of cancer. (Cho, 2007, *Molecular Cancer* 6:25)

Another recent review article on cancer biomarkers contains the following comments:

> With the emergence of genomic profiling technologies and selective molecular targeted therapies, biomarkers play an increasingly important role in the clinical management of cancer patients. Single gene/protein or multi-gene "signature"-based assays have been introduced to measure specific molecular pathway deregulations that guide therapeutic decision-making as predictive biomarkers. Genome-based prognostic biomarkers are also available for several cancer types for potential incorporation into clinical prognostic staging systems or practice guidelines. However, there is still a large gap between initial biomarker discovery studies and their clinical translation due to the challenges in the process of cancer biomarker development. (Goosens et al., *Transl. Cancer Res.* 2015 4(3):256-269)

Comments such as the foregoing illustrate the recognition of a need for the discovery of clinically useful biomarkers that can assist physicians in determining the most optimal course of treatment for cancer patients.

With respect to cancer immunotherapies, some, but not all, patients respond to a particular drug. Accordingly, there is a need to understand which biomarkers in a patient's genome may be relevant in determining if a patient will respond to a particular immunotherapy. For example, PD-L1, the ligand for PD-1, is highly expressed in several cancers; PD-1 is expressed, for example, on T-cells. Inhibition of the interaction between PD-1 and its ligand can enhance immune response and improve anti-tumor activity. However, not all patients respond to treatment with an anti-PDL1 or anti-PD1 therapy, e.g., an anti-PDL1 antibody or an anti-PD1 antibody. Therefore, there is a need for diagnostic methods based on predictive biomarkers for identifying patients with cancers that are likely (or unlikely) to respond to treatment with an immunotherapy, for example, a PDL1 or PD1 inhibitor such as an anti-PDL1 or anti-PD1 antibody.

Further, there is a need in the art to identify biomarkers that have the ability to predict whether or not a patient is likely to have a toxic response to a given immunotherapy so that medical professionals can determine the best course of treatment prior to administration and patients can avoid toxic responses to such therapies. For example, there is a need in the art to identify biomarkers that will assist in predicting the toxicity of a given immunotherapy in a patient, for example, an anti-PDL1 or anti-PD1 therapy (e.g., an anti-PDL1 antibody or an anti-PD1 antibody) or radiation. Even if a patient would respond to such a therapy, if the therapy would be toxic to that patient, it would be helpful for doctors to know this in advance and take the likely toxicity response into consideration when determining whether a given immunotherapy is appropriate for a patient.

There is a particular need to identify biomarkers found in the patient's germ-line or that are inherited that predict a patient's systemic response to immunotherapy in order to predict a patient's systemic response (both therapeutic and toxicity related) to such therapies without having to characterize a patient's specific tumor DNA.

SUMMARY

The invention is based, in part, on the discovery that cancer patients carrying one or more specified mutations in their genome may respond to treatment with an immune modulating agent more effectively than other cancer patients, for example, patients homozygous for the wild-type allele. The invention is also based, in part, on the discovery that cancer patients carrying one or more specified mutations in their genome may respond to treatment with an immune modulating agent less effectively than other patients, for example, cancer patients homozygous for the wild-type allele.

The invention is also based, in part, on the discovery that some cancer patients may have a toxic response to an immune modulating therapy as compared to other cancer patients, for example, patients homozygous for the wild-type allele who do not experience a toxic response. The invention is also based, in part, on the discovery that cancer patients carrying one or more specified mutations in their genome may not experience a toxic response to an immune modulating agent as compared to other patients, for example, patients homozygous for the wild-type allele, who do experience a toxic response.

In one aspect, the invention provides a method of treating cancer that includes administering an immune modulating agent to a patient identified as not carrying a G nucleotide at a position corresponding to position 101 of SEQ ID NO:2 (CD274/rs4742098).

In another aspect, the invention provides a method of treating cancer that includes administering an immune modulating agent to a patient identified as carrying an A nucleotide at a position corresponding to position 101 of SEQ ID NO:7 (IL18R1/rs11465660).

In another aspect, the invention provides a method of treating cancer that includes administering an immune modulating agent to a patient identified as not carrying a deletion of a T nucleotide at a position corresponding to position 101 of SEQ ID NO:19 (EXO1/rs4150021).

In another aspect, the invention provides a method of treating cancer that includes administering an immune modulating agent to a cancer patient identified as not heterozygous for an A nucleotide at a position corresponding to position 101 of SEQ ID NO:1 (CD44/rs11821102). In a further embodiment, the patient is also identified as heterozygous for an A nucleotide at a position corresponding to position 101 of SEQ ID NO:7 (IL18R1/rs11465660).

In another embodiment, the invention provides a method of treating cancer that includes administering an immune modulating agent to a cancer patient identified as not heterozygous for an A nucleotide at a position corresponding to position 101 of SEQ ID NO:1 (CD44/rs11821102), where the patient is further identified as not heterozygous for an A nucleotide at a position corresponding to position 101 of SEQ ID NO:7 (IL18R1/rs11465660) and as not homozygous for a C nucleotide at a position corresponding to position 101 of SEQ ID NO:8 (miR99a promoter). In a further embodiment, the patient is identified as heterozygous for a deletion of a T nucleotide at a position corresponding to position 101 of SEQ ID NO:19 (EXO1/rs4150021), whereas in another embodiment, the patient is identified as not heterozygous for a deletion of a T nucleotide at a position corresponding to position 101 of SEQ ID NO:19 (EXO1/rs4150021).

In another embodiment, the invention provides a method of treating cancer that includes administering an immune modulating agent to a cancer patient identified as carrying or not carrying one or more of the following mutations:
  a) an A nucleotide at a position corresponding to position 101 of SEQ ID NO:1 (CD44/rs11821102);
  b) a G nucleotide at a position corresponding to position 101 of SEQ ID NO:2 (CD274/rs4742098); or
  c) a deletion of a T nucleotide at a position corresponding to position 101 of SEQ ID NO:19 (EXO1/rs4150021);
  d) an A nucleotide at a position corresponding to position 101 of SEQ ID NO:4 (IL8/rs4073);
  e) a G nucleotide at a position corresponding to position 101 of SEQ ID NO:5 (IL10/rs3024496);
  f) a G nucleotide at a position corresponding to position 101 of SEQ ID NO:6 (IL10RB/rs2834167);
  g) an A nucleotide at a position corresponding to position 101 of SEQ ID NO:7 (IL18R1/rs11465660);
  h) a C nucleotide at a position corresponding to position 101 of SEQ ID NO:8 (miR99a promoter);
  i) an A nucleotide at a position corresponding to position 101 of SEQ ID NO:9 (RAD23A/rs8240); or
  j) a C nucleotide at a position corresponding to position 101 of SEQ ID NO:10 (STAT3/rs3744483).

In one embodiment, the patient is identified as not carrying one or more mutations selected from
  a) an A nucleotide at a position corresponding to position 101 of SEQ ID NO:1 (CD44/rs11821102);
  b) a G nucleotide at a position corresponding to position 101 of SEQ ID NO:2 (CD274/rs4742098);
  c) a deletion of a T nucleotide at a position corresponding to position 101 of SEQ ID NO:19 (EXO1/rs4150021);
  d) an A nucleotide at a position corresponding to position 101 of SEQ ID NO:4 (IL8/rs4073);
  e) a G nucleotide at a position corresponding to position 101 of SEQ ID NO:6 (IL10RB/rs2834167); or
  f) a C nucleotide at a position corresponding to position 101 of SEQ ID NO:8 (miR99a promoter).

In yet another embodiment, the patient is identified as carrying one or more mutations selected from
  a) an A nucleotide at a position corresponding to position 101 of SEQ ID NO:4 (IL8/rs4073);
  b) a G nucleotide at a position corresponding to position 101 of SEQ ID NO:5 (IL10/rs3024496);
  c) an A nucleotide at a position corresponding to position 101 of SEQ ID NO:7 (IL18R1/rs11465660);
  d) an A nucleotide at a position corresponding to position 101 of SEQ ID NO:9 (RAD23A/rs8240); or
  e) a C nucleotide at a position corresponding to position 101 of SEQ ID NO:10 (STAT3/rs3744483).

In yet another embodiment, the invention provides a method of determining a cancer patient's responsiveness to treatment with an immune modulating agent. The method includes determining whether or not the patient is heterozygous for an A nucleotide at a position corresponding to position 101 of SEQ ID NO:1 (CD44/rs11821102). Not being heterozygous for an A nucleotide at a position corresponding to position 101 of SEQ ID NO:1 (CD44/rs11821102) indicates that the patient has an increased probability of responding to the agent. In a further embodiment, the method also includes determining whether or not the patient is heterozygous for an A nucleotide at a position corresponding to position 101 of SEQ ID NO:7 (IL18R1/rs11465660). Being heterozygous for an A nucleotide at a position corresponding to position 101 of SEQ ID NO:7 (IL18R1/rs11465660) indicates that the patient has an increased probability of responding to the agent.

In yet another embodiment, the invention provides a method of determining a cancer patient's responsiveness to treatment with an immune modulating agent, which includes determining whether or not the patient is heterozygous for an A nucleotide at a position corresponding to position 101 of SEQ ID NO:1 (CD44/rs11821102), whether or not the patient is heterozygous for an A nucleotide at a position corresponding to position 101 of SEQ ID NO:7 (IL18R1/ rs11465660), and whether or not the patient is homozygous for a C nucleotide at a position corresponding to position 101 of SEQ ID NO:8 (miR99a promoter). Not being heterozygous for an A nucleotide at a position corresponding to position 101 of SEQ ID NO:1 (CD44/rs11821102), being not heterozygous for an A nucleotide at a position corresponding to position 101 of SEQ ID NO:7 (IL18R1/rs11465660), and being not homozygous for a C nucleotide at a position corresponding to position 101 of SEQ ID NO:8 (miR99a promoter) indicates that the patient has an increased probability of responding to the agent. In a further embodiment, the method includes determining whether or not the patient is heterozygous for a deletion of a T nucleotide at a position corresponding to position 101 of SEQ ID NO:19 (EXO1/rs4150021), wherein in one embodiment, being heterozygous for a deletion of a T nucleotide at a position corresponding to position 101 of SEQ ID NO:19 (EXO1/rs4150021) indicates that the patient has an increased probability of responding to the therapy, whereas in another embodiment being not heterozygous for a deletion of a T nucleotide occurring in the wild-type sequence at a position corresponding to position 101 of SEQ ID NO:19 (EXO1/rs4150021) indicates that the patient has an increased probability of responding to the agent.

In a further embodiment, the invention provides a method of determining a cancer patient's responsiveness to treatment with an immune modulating agent, which includes determining whether or not the patient carries one or more of the following mutations:
   a) an A nucleotide at a position corresponding to position 101 of SEQ ID NO:1 (CD44/rs11821102);
   b) a G nucleotide at a position corresponding to position 101 of SEQ ID NO:2 (CD274/rs4742098);
   c) a deletion of a T nucleotide at a position corresponding to position 101 of SEQ ID NO:19 (EXO1/rs4150021);
   d) an A nucleotide at a position corresponding to position 101 of SEQ ID NO:4 (IL8/rs4073);
   e) a G nucleotide at a position corresponding to position 101 of SEQ ID NO:5 (IL10/rs3024496);
   f) a G nucleotide at a position corresponding to position 101 of SEQ ID NO:6 (IL1 ORB/rs2834167);
   g) an A nucleotide at a position corresponding to position 101 of SEQ ID NO:7 (IL18R1/rs11465660);
   h) a C nucleotide at a position corresponding to position 101 of SEQ ID NO:8 (miR99a promoter);
   i) an A nucleotide at a position corresponding to position 101 of SEQ ID NO:9 (RAD23A/rs8240); or
   j) a C nucleotide at a position corresponding to position 101 of SEQ ID NO:10 (STAT3/rs3744483).

In one embodiment, if the patient does not carry one or more of the following mutations
   a) an A nucleotide at a position corresponding to position 101 of SEQ ID NO:1 (CD44/rs11821102);
   b) a G nucleotide at a position corresponding to position 101 of SEQ ID NO:2 (CD274/rs4742098);
   c) a deletion of a T nucleotide occurring in the wild-type sequence at a position corresponding to position 101 of SEQ ID NO:19 (EXO1/rs4150021);
   d) an A nucleotide at a position corresponding to position 101 of SEQ ID NO:4 (IL8/rs4073);
   e) a G nucleotide at a position corresponding to position 101 of SEQ ID NO:6 (IL10RB/rs2834167); or
   f) a C nucleotide at a position corresponding to position 101 of SEQ ID NO:8 (mir99a promoter), the patient has an increased probability of responding to the agent.

In another embodiment, if the patient carries one or more of the following mutations,
   a) an A nucleotide at a position corresponding to position 101 of SEQ ID NO:4 (IL8/rs4073);
   b) a G nucleotide at a position corresponding to position 101 of SEQ ID NO:5 (IL10/rs3024496);
   c) an A nucleotide at a position corresponding to position 101 of SEQ ID NO:7 (IL18R1/rs11465660);
   d) an A nucleotide at a position corresponding to position 101 of SEQ ID NO:9 (RAD23A/rs8240); or
   e) a C nucleotide at a position corresponding to position 101 of SEQ ID NO:10 (STAT3/rs3744483), the patient has an increased probability of responding to the immune modulating agent.

In any of the aforementioned embodiments of the invention, the cancer may be melanoma or lung cancer, or in other embodiments, the cancer may be melanoma (including non-resectable or metastatic melanoma), lung cancer (including non-small cell lung cancer and metastatic non-small cell lung cancer), adrenal cancer, anal cancer, bile duct cancer, bladder cancer, bone cancer, cancer of the brain or central nervous system, basal cell skin cancer, breast cancer, cervical cancer, colon cancer, colorectal cancer, endometrial cancer, esophageal cancer, eye cancer, gallbladder cancer, gastrointestinal carcinoid tumors, gastrointestinal stromal tumor (GIST), gastric cancer, glioma, glioblastoma, head and neck cancer (including head and neck squamous cell carcinoma), Hodgkin disease, Classical Hodgkin Lymphoma, diffuse large B cell lymphoma, follicular lymphoma, Kaposi sarcoma, kidney cancer, laryngeal and hypopharyngeal cancer, leukemia (including acute myeloid leukemia), liver cancer (including hepatocellular carcinoma), lymphoma, malignant mesothelioma, merkel cell carcinoma, metastatic urothelial carcinoma, multiple myeloma, myeloma, myelodysplastic syndrome, nasal cavity and paranasal sinus cancer, nasopharyngeal cancer, neuroendocrine cancer, neuroblastoma, non-Hodgkin lymphoma, oral cavity and oropharyngeal cancer, osteosarcoma, ovarian cancer, pancreatic cancer, penile cancer, pituitary tumors, prostate cancer, renal cancer (including renal cell carcinoma), retinoblastoma, rhabdomyosarcoma, salivary gland cancer, sarcoma, squamous cell skin cancer, small intestine cancer, stomach cancer, testicular cancer, thymus cancer, thyroid cancer, uterine cancer, or vaginal cancer.

In any of the aforementioned embodiments of the invention, immune modulating therapy may be an anti-PDL1 or anti-PD1 antibody or portion thereof.

In any of the aforementioned embodiments of the invention, the patient can be progression free six months after beginning the treatment with the immune modulating agent In any of the aforementioned embodiments of the invention, the patient is preferably a human patient. The human patient may be a male or female patient.

In another aspect, the invention provides a reduced-toxicity method of cancer treatment including administering an immune modulating agent to a patient suffering from cancer, wherein the patient is identified as not carrying an A nucleotide at a position corresponding to position 101 of SEQ ID NO:15 (RAC1/rs9374).

In another aspect, the invention provides a reduced-toxicity method of cancer treatment including administering an immune modulating agent to a patient suffering from cancer, wherein the patient is identified as carrying a G nucleotide at a position corresponding to position 101 of SEQ ID NO:14 (KRAS/rs61764370).

In another aspect, the invention provides a reduced-toxicity method of cancer treatment including administering an immune modulating agent to a patient suffering from cancer where the patient is identified as neither heterozygous nor homozygous for a C nucleotide at a position corresponding to position 101 of SEQ ID NO:12 (FCGR2A/rs10919033). In a further embodiment, the patient is also identified as neither heterozygous nor homozygous for a G nucleotide at a position corresponding to position 101 of SEQ ID NO:16 (TLR4/rs4986790).

In another aspect, the invention provides a reduced-toxicity method of cancer treatment including administering an immune modulating agent to a patient suffering from cancer where the patient is identified as neither heterozygous nor homozygous for a C nucleotide at a position corresponding to position 101 of SEQ ID NO:12 (FCGR2A/rs10919033) and identified as heterozygous or homozygous for a G nucleotide at a position corresponding to position 101 of SEQ ID NO:14 (KRAS/rs61764370). In a further embodiment, the patient is also identified as neither heterozygous nor homozygous for a G nucleotide at a position corresponding to position 101 of SEQ ID NO:16 (TLR4/rs4986790).

In another aspect, the invention provides a reduced-toxicity method of cancer treatment including administering an immune modulating agent to a patient suffering from cancer where the patient is identified as carrying or not carrying one or more of the following mutations:
  a. a G nucleotide at a position corresponding to position 101 of SEQ ID NO:11 (EREG/rs1460008);
  b. a C nucleotide at a position corresponding to position 101 of SEQ ID NO:12 (FCGR2A/rs10919033);
  c. a C nucleotide at a position corresponding to position 101 of SEQ ID NO:13 (FCGR2A/rs1801274);
  d. a G nucleotide at a position corresponding to position 101 of SEQ ID NO:6 (IL10RB/rs2834167);
  e. a G nucleotide at a position corresponding to position 101 of SEQ ID NO:14 (KRAS/rs61764370);
  f. a C nucleotide at a position corresponding to position 101 of SEQ ID NO:8 (miR99a promoter);
  g. an A nucleotide at a position corresponding to position 101 of SEQ ID NO:15 (RAC1/rs9374);
  h. a G nucleotide at a position corresponding to position 101 of SEQ ID NO:16 (TLR4/rs4986790);
  i. a G nucleotide at a position corresponding to position 101 of SEQ ID NO:2 (CD274/rs4742098); or
  j. a C nucleotide at a position corresponding to position 101 of SEQ ID NO:33 (MSH2/rs2303428).

In a further embodiment, the immune modulating therapy is an anti-PD1 or anti-PDL1 antibody. According to this embodiment, the patient is identified as not carrying one or more of the following mutations:
  a) a G nucleotide at a position corresponding to position 101 of SEQ ID NO:11 (EREG/rs1460008);
  b) a C nucleotide at a position corresponding to position 101 of SEQ ID NO:12 (FCGR2A/rs10919033);
  c) an A nucleotide at a position corresponding to position 101 of SEQ ID NO:15 (RAC1/rs9374);
  d) a G nucleotide at a position corresponding to position 101 of SEQ ID NO:16 (TLR4/rs4986790); or
  e) a G nucleotide at a position corresponding to position 101 of SEQ ID NO:2 (CD274/rs4742098),
whereas in yet a further embodiment, the patient is identified as carrying one or more of the following mutations:
  a) a C nucleotide at a position corresponding to position 101 of SEQ ID NO:13 (FCGR2A/rs1801274);
  b) a G nucleotide at a position corresponding to position 101 of SEQ ID NO:6 (IL10RB/rs2834167);
  c) a G nucleotide at a position corresponding to position 101 of SEQ ID NO:14 (KRAS/rs61764370);
  d) a C nucleotide at a position corresponding to position 101 of SEQ ID NO:8 (miR99a promoter); or
  e) a C nucleotide at a position corresponding to position 101 of SEQ ID NO:33 (MSH2/rs2303428).

In a further embodiment, the immune modulating therapy is radiation. In such embodiments, the patient is identified as having one or more of the following mutations:
  a. a G nucleotide at a position corresponding to position 101 of SEQ ID NO:16 (TLR4/rs4986790);
  b. a G nucleotide at a position corresponding to position 101 of SEQ ID NO:2 (CD274/rs4742098); or
  c. a G nucleotide at a position corresponding to position 101 of SEQ ID NO:6 (IL10RB/rs2834167),
whereas in a further embodiment, the patient is identified as having one or more of the following genotypes:
  a) heterozygous or homozygous for a G nucleotide at a position corresponding to position 101 of SEQ ID NO:16 (TLR4/rs4986790);
  b) not homozygous for a G nucleotide at a position corresponding to position 101 of SEQ ID NO:2 (CD274/rs4742098); or
  c) not homozygous for a G nucleotide at a position corresponding to position 101 of SEQ ID NO:6 (IL10RB/rs2834167).

In one embodiment, the radiation may be external beam radiation therapy, while in another embodiment, the radiation is brachytherapy, while in another embodiment, the radiation may be stereotactic body radiation therapy (SBRT).

In another embodiment, the invention provides a method for determining the toxicity of an immune modulating agent in a cancer patient. The method includes determining whether the patient is heterozygous or homozygous for a C nucleotide at a position corresponding to position 101 of SEQ ID NO:12 (FCGR2A/rs10919033). If the patient is neither heterozygous nor homozygous for a C nucleotide at a position corresponding to position 101 of SEQ ID NO:12 (FCGR2A/rs10919033), the patient has a decreased likelihood of a toxic response to the immune modulating agent. In a further embodiment, it is also determined whether the patient is heterozygous or homozygous for a G nucleotide at a position corresponding to position 101 of SEQ ID NO:16 (TLR4/rs4986790). If the patient is neither heterozygous nor homozygous for an G nucleotide at a position corresponding to position 101 of SEQ ID NO:16 (TLR4/rs4986790), the patient has a decreased likelihood of a toxic response to the immune modulating agent.

In another embodiment, the invention provides a method for determining the toxicity of an immune modulating agent in a cancer patient. The method includes determining whether the patient is heterozygous or homozygous for a C nucleotide at a position corresponding to position 101 of SEQ ID NO:12 (FCGR2A/rs10919033) and whether the patient is heterozygous or homozygous for a G nucleotide at a position corresponding to position 101 of SEQ ID NO:14 (KRAS/rs61764370). If the patient is neither heterozygous nor homozygous for a C nucleotide at a position corresponding to position 101 of SEQ ID NO:12 (FCGR2A/rs10919033) and is heterozygous or homozygous for a G nucleotide at a position corresponding to position 101 of SEQ ID NO:14 (KRAS/rs61764370), the patient has a decreased likelihood of a toxic response to the immune modulating agent. In a further embodiment, it is determined if the patient is heterozygous or homozygous for a G nucleotide at a position corresponding to position 101 of SEQ ID NO:16 (TLR4/rs4986790). If the patient is neither heterozygous nor homozygous for a G nucleotide at a position corresponding to position 101 of SEQ ID NO:16 (TLR4/rs4986790), the patient has a decreased likelihood of a toxic response to the immune modulating agent.

The invention also provides a method for determining the toxicity of an immune modulating agent in a cancer patient. The method includes determining whether the patient carries one or more mutations selected from the group consisting of:
a) a G nucleotide at a position corresponding to position 101 of SEQ ID NO:11 (EREG/rs1460008);
b) a C nucleotide at a position corresponding to position 101 of SEQ ID NO:12 (FCGR2A/rs10919033);
c) a C nucleotide at a position corresponding to position 101 of SEQ ID NO:13 (FCGR2A/rs1801274);
d) a G nucleotide at a position corresponding to position 101 of SEQ ID NO:6 (IL10RB/rs2834167);
e) a G nucleotide at a position corresponding to position 101 of SEQ ID NO:14 (KRAS/rs61764370);
f) a C nucleotide at a position corresponding to position 101 of SEQ ID NO:8 (miR99a promoter);
g) an A nucleotide at a position corresponding to position 101 of SEQ ID NO:15 (RAC1/rs9374);
h) a G nucleotide at a position corresponding to position 101 of SEQ ID NO:16 (TLR4/rs4986790);
i) a G nucleotide at a position corresponding to position 101 of SEQ ID NO:2 (CD274/rs4742098) and
j) a C nucleotide at a position corresponding to position 101 of SEQ ID NO:33 (MSH2/rs2303428).

In one embodiment, the immune modulating agent is an anti-PD1 or anti-PDL1 antibody. In such an embodiment, if the patient does not carry one or more of the mutations selected from
a) a G nucleotide at a position corresponding to position 101 of SEQ ID NO:11 (EREG/rs1460008);
b) a C nucleotide at a position corresponding to position 101 of SEQ ID NO:12 (FCGR2A/rs10919033);
c) an A nucleotide at a position corresponding to position 101 of SEQ ID NO:15 (RAC1/rs9374);
d) a G nucleotide at a position corresponding to position 101 of SEQ ID NO:16 (TLR4/rs4986790); or
e) a G nucleotide at a position corresponding to position 101 of SEQ ID NO:2 (CD274/rs4742098),
the patient has a decreased likelihood of a toxic response to the agent, whereas in another such embodiment, if the patient carries one or more of the mutations selected from
a) a C nucleotide at a position corresponding to position 101 of SEQ ID NO:13 (FCGR2A/rs1801274);
b) a G nucleotide at a position corresponding to position 101 of SEQ ID NO:6 (IL10RB/rs2834167);
c) a G nucleotide at a position corresponding to position 101 of SEQ ID NO:14 (KRAS/rs61764370);
d) a C nucleotide at a position corresponding to position 101 of SEQ ID NO:8 (miR99a promoter); or
e) a C nucleotide at a position corresponding to position 101 of SEQ ID NO:33 (MSH2/rs2303428).

In yet another embodiment, the immune modulating agent is radiation therapy. In such an embodiment, it is determined if the patient carries one or more of the following mutations:
a) a G nucleotide at a position corresponding to position 101 of SEQ ID NO:16 (TLR4/rs4986790);
b) a G nucleotide at a position corresponding to position 101 of SEQ ID NO:2 (CD274/rs4742098); and/or
c) a G nucleotide at a position corresponding to position 101 of SEQ ID NO:6 (IL10RB/rs2834167),
whereas in a further such embodiment, it is determined whether the patient has one or more of the following genotypes:
a) heterozygous or homozygous for a G nucleotide at a position corresponding to position 101 of SEQ ID NO:16 (TLR4/rs4986790);
b) not homozygous for a G nucleotide at a position corresponding to position 101 of SEQ ID NO:2 (CD274/rs4742098); or
c) not homozygous for a G nucleotide at a position corresponding to position 101 of SEQ ID NO:6 (IL10RB/rs2834167);
wherein if the patient has one of these genotypes, the patient is consider as having a decreased likelihood of a toxic response to the radiation.

In one embodiment, the radiation is external beam radiation, whereas in another embodiment, the radiation is stereotactic body radiation therapy, whereas in another embodiment, the radiation is brachytherapy.

In any of the aforementioned embodiments of the invention, the cancer may be melanoma or lung cancer, or in other embodiments, the cancer may be melanoma (including non-resectable or metastatic melanoma), lung cancer (including non-small cell lung cancer and metastatic non-small cell lung cancer), adrenal cancer, anal cancer, bile duct cancer, bladder cancer, bone cancer, cancer of the brain or central nervous system, basal cell skin cancer, breast cancer, cervical cancer, colon cancer, colorectal cancer, endometrial cancer, esophageal cancer, eye cancer, gallbladder cancer, gastrointestinal carcinoid tumors, gastrointestinal stromal tumor (GIST), gastric cancer, glioma, glioblastoma, head and neck cancer (including head and neck squamous cell carcinoma), Hodgkin disease, Classical Hodgkin Lymphoma, diffuse large B cell lymphoma, follicular lymphoma, Kaposi sarcoma, kidney cancer, laryngeal and hypopharyngeal cancer, leukemia (including acute myeloid leukemia), liver cancer (including hepatocellular carcinoma), lymphoma, malignant mesothelioma, merkel cell carcinoma, metastatic urothelial carcinoma, multiple myeloma, myeloma, myelodysplastic syndrome, nasal cavity and paranasal sinus cancer, nasopharyngeal cancer, neuroendocrine cancer, neuroblastoma, non-Hodgkin lymphoma, oral cavity and oropharyngeal cancer, osteosarcoma, ovarian cancer, pancreatic cancer, penile cancer, pituitary tumors, prostate cancer, renal cancer (including renal cell carcinoma), retinoblastoma, rhabdomyosarcoma, salivary gland cancer, sarcoma, squamous cell skin cancer, small intestine cancer, stomach cancer, testicular cancer, thymus cancer, thyroid cancer, uterine cancer, or vaginal cancer.

In any of the aforementioned embodiments of the invention, the patient is preferably a human patient. The human patient may be a male or female patient.

BRIEF DESCRIPTION OF THE DRAWINGS

FIG. 1 is a table showing single nucleotide mutations found in various human genes and the corresponding wild-type sequences. As described herein, these mutations are biomarkers that are relevant to predicting a patient's systemic response (both therapeutic and toxic) to treatment with an immune modulating agent. The sequences shown are segments of the human gene's nucleotide sequence; 100 nucleotides upstream (5') and 100 nucleotides downstream (3') of the mutation are shown. The mutation is shown in square brackets "[ ]" in the variant sequence and is at position 101; the corresponding wild-type nucleotide is shown in square brackets "[ ]" at position 101 in the wild-type sequence. SEQ ID NOS: 1-16 and 33 are the variant sequences while SEQ ID NOS: 17-32 and 34 are the wild-type version of the sequence (i.e., without the mutation).

DETAILED DESCRIPTION OF THE INVENTION

Single Nucleotide Germ-Line Mutations as Biomarkers

Figure 2:
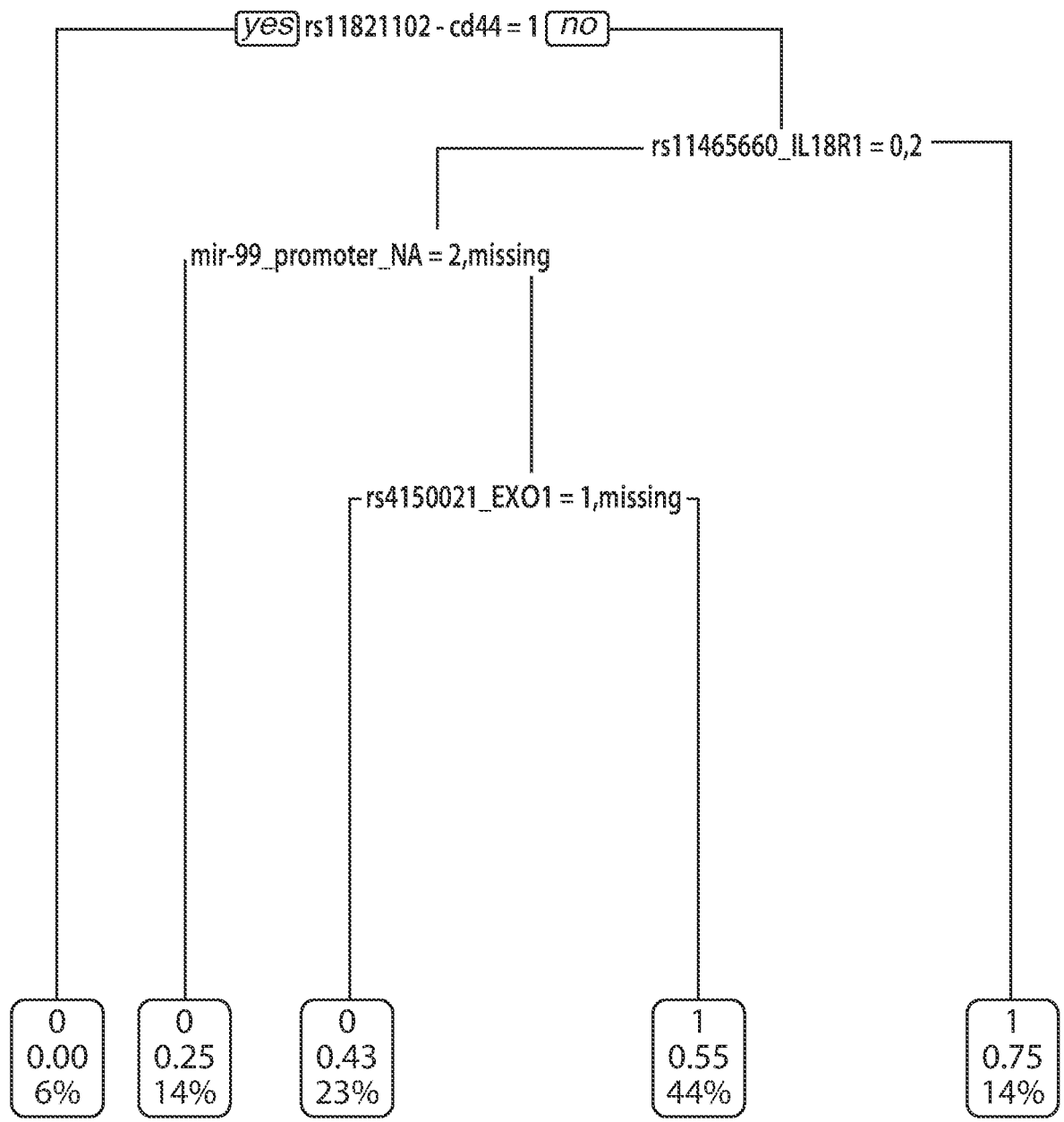
FIG. 2 is a tree-based classification rule providing a prognostic indication of a patient's response to treatment with an immune modulating agent. Each leaf of the tree provides a probability of response to treatment based on the presence of absence of the particular biomarker as indicated therein, i.e., CD44/rs11821102, IL18R1/rs11465660, miR99a promoter, and EXO1/rs4150021. "0" means the patient is homozygous wild-type. "1" means the patient carries one copy of the mutation, i.e., the patient is heterozygous for the mutation. "2" means the patient is homozygous for the mutation. "Missing" means no data is available for the patient.

The invention is based, in part, on the discovery that a cancer patient carrying one or more specified mutations in their genome may respond to an immune modulating agent more effectively than other patients, e.g., wild-type patients. The invention is also based, in part, on the discovery that a cancer patient carrying one or more specified mutations in their genome may respond to an immune modulating agent less effectively than other patients, e.g., wild-type patients. While these mutations may commonly be referred to as single nucleotide polymorphisms or "SNPs," the mutations disclosed herein are functional mutations that are present in the germ-line. The mutations are generally to a single nucleotide, for example, substitution of a nucleotide or deletion of a nucleotide.

The mutations referred to herein include functional mutations that disrupt microRNA pathways, and include microRNA binding site mutations. A microRNA (miRNA) is a small non-coding RNA molecule containing about 22 nucleotides found in plants, animals, and some viruses that functions in RNA silencing and post-transcription regulation of gene expression. These functions are integral to miRNAs' role as critical stress response mediators, including mediating the immune and inflammatory response. DNA damage is also known to cause changes in the global profile of miRNA expression (Weidhaas et al., Cancer Res, 2007, 67:11111) and stress-induced miRNA deregulation has been observed at the level of transcription, processing, subcellular localization and functioning. Accordingly, biomarkers predictive of disruption in microRNA pathways may be useful for predicting systemic immune response to immune modulating therapies as well as toxicity of such therapies, particularly because of how such pathways influence immune and inflammatory response. Further, because immune therapy for treating cancer relies on modulating the immune response in a patient, and irAE toxicity to immune therapy results from immune response, it is believed that markers disclosed herein as relevant to predicting response to an immune modulating agent are also relevant to predicting a patient's likelihood of having a toxic response to an immune modulating agent.

As described in the examples herein, several mutations have been identified as being pertinent to determining a cancer patient's likelihood of responding to an immune modulating agent for treatment of cancer. These mutations (also referred to herein as "markers," "biomarkers," or "variants") are shown in SEQ ID NOS: 1-10 of FIG. 1 as the nucleotides in square brackets.

One biomarker relevant to determining a cancer patient's response to an immune modulating agent is found in the human CD44 gene; the marker is a SNP defined as rs11821102. In FIG. 1, 100 nucleotides upstream (5') of the mutation and 100 nucleotides downstream (3') of the mutation are shown. The mutation is an A nucleotide (variant) substituted in place of a G nucleotide (wild-type). The mutation occurs at position 101 of SEQ ID NO:1 (variant sequence) or SEQ ID NO:17 (wild-type sequence). In one embodiment, a patient identified as not carrying this polymorphism is identified as having an increased likelihood of response to treatment with an immune modulating agent, whereas a patient identified as carrying the polymorphism is identified as having a decreased likelihood of response to treatment with an immune modulating agent. In another embodiment, a patient who does not carry the CD44 mutation or who is homozygous for the CD44 mutation has an increased likelihood of response to an immune modulating agent as compared to a patient who is heterozygous for the CD44 mutation. In one embodiment, a patient who is heterozygous for the CD44 mutation is considered a non-responder.

Another biomarker relevant to determining a cancer patient's response to an immune modulating agent is found in the human CD274 gene; the marker is a SNP defined as rs4742098. In FIG. 1, 100 nucleotides upstream (5') of the mutation and 100 nucleotides downstream (3') of the mutation are shown. The mutation is a G nucleotide (variant) substituted in place of an A nucleotide (wild-type). The mutation occurs at position 101 of SEQ ID NO:2 (variant sequence) or SEQ ID NO:18 (wild-type sequence). In one embodiment, a patient identified as not carrying this polymorphism is identified as having an increased likelihood of response to treatment with an immune modulating agent, whereas a patient identified as carrying the polymorphism is identified as having a decreased likelihood of response to treatment with an immune modulating agent.

Another biomarker relevant to determining a cancer patient's response to an immune modulating agent is found in the human EXO1 gene; the marker is a SNP defined as rs4150021. In FIG. 1, 100 nucleotides upstream (5') of the mutation and 100 nucleotides downstream (3') of the mutation are shown. The mutation is the deletion of the T nucleotide (variant) at position 101 of the wild-type sequence, SEQ ID NO:19. In one embodiment, a patient identified as not carrying this mutation is identified as having an increased likelihood of response to treatment with an immune modulating agent, whereas a patient identified as carrying the mutation is identified as having a decreased likelihood of response to treatment with an immune modulating agent. In another embodiment, a patient who does not carry the EXO1 mutation or who is homozygous for the EXO1 mutation has an increased likelihood of response as compared to a patient who is heterozygous for the EXO1 mutation. In another embodiment, a patient who is heterozygous for the EXO1 mutation would be predicted as being a medium responder, as opposed to a responder or strong responder.

Another biomarker relevant to determining a cancer patient's response to an immune modulating agent is found in the human IL8 gene; the marker is a SNP defined as rs4073. In FIG. 1, 100 nucleotides upstream (5') of the mutation and 100 nucleotides downstream (3') of the mutation are shown. The mutation is an A nucleotide (variant) substituted in place of a T nucleotide (wild-type). The mutation occurs at position 101 of SEQ ID NO:4 (variant sequence) or SEQ ID NO:20 (wild-type sequence). In one embodiment, a patient identified as carrying this mutation is identified as having an increased likelihood of response to treatment with an immune modulating agent, whereas a patient identified as not carrying the mutation is identified as having a decreased likelihood of response to treatment with an immune modulating agent.

Another biomarker relevant to determining a cancer patient's response to an immune modulating agent is found in the human IL10 gene; the marker is a SNP defined as rs3024496. In FIG. 1, 100 nucleotides upstream (5') of the mutation and 100 nucleotides downstream (3') of the mutation are shown. The mutation is a G nucleotide (variant) substituted in place of an A nucleotide (wild-type). The mutation occurs at position 101 of SEQ ID NO:5 (variant sequence) or SEQ ID NO:21 (wild-type sequence). In one embodiment, a patient identified as carrying this mutation is identified as one who having an increased likelihood of response to treatment with an immune modulating agent, whereas a patient identified as not carrying the mutation is identified as having a decreased likelihood of response to treatment with an immune modulating agent.

Another biomarker relevant to determining a cancer patient's response to an immune modulating agent is found in the human IL10RB gene; the marker is a SNP defined as rs2834167. In FIG. 1, 100 nucleotides upstream (5') of the mutation and 100 nucleotides downstream (3') of the mutation are shown. The mutation is a G nucleotide (variant) substituted in place of an A nucleotide (wild-type). The mutation occurs at position 101 of SEQ ID NO:6 (variant sequence) or SEQ ID NO:22 (wild-type sequence). In one embodiment, a patient identified as not carrying this mutation is identified as having an increased likelihood of response to treatment with an immune modulating agent, whereas a patient identified as carrying the mutation is identified as having a decreased likelihood of response to treatment with an immune modulating agent.

Another biomarker relevant to determining a cancer patient's response to an immune modulating agent is found in the human IL18R1 gene; the marker is a SNP defined as rs11465660. In FIG. 1, 100 nucleotides upstream (5') of the mutation and 100 nucleotides downstream (3') of the mutation are shown. The mutation is an A nucleotide (variant) substituted in place of a C nucleotide (wild-type). The mutation occurs at position 101 of SEQ ID NO:7 (variant sequence) or SEQ ID NO:23 (wild-type sequence). In one embodiment, a patient identified as carrying this mutation is identified as one who having an increased likelihood of response to treatment with an immune modulating agent, whereas a patient identified as not carrying the mutation is identified as having a decreased likelihood of response to treatment with an immune modulating agent. In another embodiment, a patient who is heterozygous for the IL18R1 mutation has an increased likelihood of response to an immune modulating agent as compared to a patient who does not carry the mutation or who is homozygous for the mutation.

Another biomarker relevant to determining a cancer patient's response to an immune modulating agent is found in the promoter region of the human miR99a gene. In FIG. 1, 100 nucleotides upstream (5') of the mutation and 100 nucleotides downstream (3') of the mutation are shown. The mutation is a C nucleotide (variant) substituted in place of a T nucleotide (wild-type). The mutation occurs at position 101 of SEQ ID NO:8 (variant sequence) or SEQ ID NO:24 (wild-type sequence). In one embodiment, a patient identified as not carrying this mutation is identified as having an increased likelihood of response to treatment with an immune modulating agent, whereas a patient identified as carrying the mutation is identified as having a decreased likelihood of response to treatment with an immune modulating agent. In another embodiment, a patient who does not carry the mir99a mutation or who is heterozygous for the mir99 mutation has an increased likelihood of response as compared to a patient who is homozygous for the mir99 mutation. In one embodiment, a patient who is homozygous for the mir99 mutation is considered a relative non-responder as compared to a patient who does not carry the mir99a mutation or who is heterozygous for the mir99 mutation.

Another biomarker relevant to determining a cancer patient's response to an immune modulating agent is found in the human RAD23A gene; the marker is a SNP defined as rs8240. In FIG. 1, 100 nucleotides upstream (5') of the mutation and 100 nucleotides downstream (3') of the mutation are shown. The mutation is an A nucleotide (variant) substituted in place of a G nucleotide (wild-type). The mutation occurs at position 101 of SEQ ID NO:9 (variant sequence) or SEQ ID NO:25 (wild-type sequence). In one embodiment, a patient identified as carrying this mutation is identified as one who having an increased likelihood of response to treatment with an immune modulating agent, whereas a patient identified as not carrying the mutation is identified as having a decreased likelihood of response to treatment with an immune modulating agent.

Another biomarker relevant to determining a cancer patient's response to an immune modulating agent is found in the human STATS gene; the marker is a SNP defined as rs3744883. In FIG. 1, 100 nucleotides upstream (5') of the mutation and 100 nucleotides downstream (3') of the mutation are shown. The mutation is a C nucleotide (variant) substituted in place of a T nucleotide (wild-type). The mutation occurs at position 101 of SEQ ID NO:10 (variant sequence) or SEQ ID NO:26 (wild-type sequence). In one embodiment, a patient identified as carrying this mutation is identified as one who having an increased likelihood of response to treatment with an immune modulating agent, whereas a patient identified as not carrying the mutation is identified as having a decreased likelihood of response to treatment with an immune modulating agent.

According to one embodiment of the invention, the aforementioned biomarkers are used to identify patients who will respond to an immune modulating agent. Accordingly, in one embodiment, it is determined whether the patient carries or does not carry one or more of the following mutations in order to determine a patient's predicted response to an immune modulating therapy:
    a) an A nucleotide at a position corresponding to position 101 of SEQ ID NO:1 (CD44/rs11821102);
    b) a G nucleotide at a position corresponding to position 101 of SEQ ID NO:2 (CD274/rs4742098); and c) a deletion of a T nucleotide at a position corresponding to position 101 of SEQ ID NO:19 (EXO1/rs4150021);
d) an A nucleotide at a position corresponding to position 101 of SEQ ID NO:4 (IL8/rs4073);
e) a G nucleotide at a position corresponding to position 101 of SEQ ID NO:5 (IL10/rs3024496);
f) a G nucleotide at a position corresponding to position 101 of SEQ ID NO:6 (IL10RB/rs2834167);
g) an A nucleotide at a position corresponding to position 101 of SEQ ID NO:7 (IL18R1/rs11465660);
h) a C nucleotide at a position corresponding to position 101 of SEQ ID NO:8 (miR99a promoter);
i) an A nucleotide at a position corresponding to position 101 of SEQ ID NO:9 (RAD23A/rs8240); and
j) a C nucleotide at a position corresponding to position 101 of SEQ ID NO:10 (STAT3/rs3744483).

In a further embodiment, it is determined if the patient does not carry one or more mutations selected from
a) an A nucleotide at a position corresponding to position 101 of SEQ ID NO:1 (CD44/rs11821102);
b) a G nucleotide at a position corresponding to position 101 of SEQ ID NO:2 (CD274/rs4742098); and
c) a deletion of a T nucleotide at a position corresponding to position 101 of SEQ ID NO:19 (EXO1/rs4150021);
d) an A nucleotide at a position corresponding to position 101 of SEQ ID NO:4 (IL8/rs4073);
e) a G nucleotide at a position corresponding to position 101 of SEQ ID NO:6 (IL10RB/rs2834167); or
f) a C nucleotide at a position corresponding to position 101 of SEQ ID NO:8 (miR99a promoter).

If the patient does not carry one or more of these mutations, the patient is predicted as having an increased probability of responding to the agent. In one embodiment, it is determined whether the patient carries one, two, three, four, five or all six of the aforementioned biomarkers in order to predict a patient's response to the immune modulating agent. For example, the determination of whether a patient has an increased probability of responding to the agent may be based on whether the patient does not carry only one, only two, only three, only four, only five, or all six, but may not require assessment of all six markers. For example, the determination of whether a patient has an increased probability of responding to the agent may be based on whether the patient does not carry at least one, at least two, at least three, or at least four, or at least five of the aforementioned six biomarkers.

In yet a further embodiment, it is determined if the patient carries one or more mutations selected from
a) an A nucleotide at a position corresponding to position 101 of SEQ ID NO:4 (IL8/rs4073);
b) a G nucleotide at a position corresponding to position 101 of SEQ ID NO:5 (IL10/rs3024496);
c) an A nucleotide at a position corresponding to position 101 of SEQ ID NO:7 (IL18R1/rs11465660);
d) an A nucleotide at a position corresponding to position 101 of SEQ ID NO:9 (RAD23A/rs8240); or
e) a C nucleotide at a position corresponding to position 101 of SEQ ID NO:10 (STAT3/rs3744483).

If the patient carries one or more of these mutations, the patient is predicted as having an increased probability of responding to the agent. In one embodiment, it is determined whether the patient carries one, two, three, four, or all five of the aforementioned biomarkers in order to predict a patient's response to the immune modulating agent. For example, the determination of whether a patient has an increased probability of responding to the agent may be based on whether the patient carries only one, only two, only three, only four, or all five, but may not require assessment of all five markers. In a further embodiment, the determination of whether a patient has an increased probability of responding to the agent may be based on whether the patient carries at least one, at least two, at least three, or at least four of the aforementioned five biomarkers.

Biomarkers predictive of response may be used either alone or in combination with one or more other biomarkers disclosed herein predictive of response to an immune modulating therapy to provide a method for predicting a patient's likely response to an immune modulating therapy. In particular, knowing whether a patient is homozygous or heterozygous for a particular marker associated with response to an immune therapy (or does not carry the marker, i.e., wild-type) can be useful in determining the patient's likely response to an immune modulating therapy.

For example, with respect to CD44/rs11821102, if the patient is not heterozygous for an A nucleotide at a position corresponding to position 101 of SEQ ID NO:1 (CD44/rs11821102), the patient has an increased likelihood of response to an immune modulating therapy.

With respect to IL18R1/rs11465660, if the patient is heterozygous for an A nucleotide at a position corresponding to position 101 of SEQ ID NO:7 (IL18R1/rs11465660), the patient has an increased likelihood of response to an immune modulating therapy.

In particular, if a patient is both not heterozygous for an A nucleotide at a position corresponding to position 101 of SEQ ID NO:1 (CD44/rs11821102) and heterozygous for an A nucleotide at a position corresponding to position 101 of SEQ ID NO:7 (IL18R1/rs11465660), the patient has an increased likelihood of response to an immune modulating therapy.

With respect to the mutation disclosed in SEQ ID NO:8 (mir99a promoter) in the human mir99a promoter, if a patient is not homozygous for a C nucleotide at a position corresponding to position 101 of SEQ ID NO:8 (mir99a promoter), the patient has an increased likelihood of response to an immune modulating therapy. This genotype is particularly indicative of response if the patient is not heterozygous for an A nucleotide at a position corresponding to position 101 of SEQ ID NO:7 (IL18R1/rs11465660). Moreover, this genotype is also particularly indicative of response if the patient is not heterozygous for an A nucleotide at a position corresponding to position 101 of SEQ ID NO:1 (CD44/rs11821102).

With respect to EXO1/rs4150021, if the patient is heterozygous for a deletion of a T nucleotide at a position corresponding to position 101 of SEQ ID NO:19 (EXO1/rs4150021), this indicates an increased likelihood of response. However, if the patient is not heterozygous for a deletion of a T nucleotide occurring in the wild-type sequence at a position corresponding to position 101 of SEQ ID NO:19 (EXO1/rs4150021), the likelihood of response will be higher than if the patient is heterozygous for the deletion. These markers are particularly predictive of an increased likelihood of response in a patient that is not homozygous for a C nucleotide at a position corresponding to position 101 of SEQ ID NO:8 (miR99a promoter). These markers are particularly predictive of an increased likelihood of response in a patient who is not heterozygous for an A nucleotide at a position corresponding to position 101 of SEQ ID NO:7 (IL18R1/rs11465660) and who is not heterozygous for an A nucleotide at a position corresponding to position 101 of SEQ ID NO:1 (CD44/rs11821102).

In one embodiment of the invention, the response of a patient to an immune modulating agent is predicted by determining the zygosity of that patient with respect to an A nucleotide at a position corresponding to position 101 of SEQ ID NO:1 (CD44/rs11821102), an A nucleotide at a position corresponding to position 101 of SEQ ID NO:7 (IL18R1/rs11465660), a C nucleotide at a position corresponding to position 101 of SEQ ID NO:8 (miR99a promoter), and a deletion of a T nucleotide occurring in the wild-type sequence at a position corresponding to position 101 of SEQ ID NO:19 (EXO1/rs4150021). The zygosity of one, two, three, or all four of these markers may be determined and assessed to predict the patient's response to the immune modulating agent.

For example, in one embodiment, a patient is assessed to determine if the patient is heterozygous or not heterozygous for an A nucleotide at a position corresponding to position 101 of SEQ ID NO:1 (CD44/rs11821102). For example, in another embodiment, a patient is assessed to determine if the patient is heterozygous or not heterozygous for an A nucleotide at a position corresponding to position 101 of SEQ ID NO:7 (IL18R1/rs11465660). For example, in another embodiment, a patient is assessed to determine if the patient is homozygous or not homozygous for a C nucleotide at a position corresponding to position 101 of SEQ ID NO:8 (miR99a promoter). In yet another embodiment, a patient is assessed to determine if the patient is heterozygous or not heterozygous for a deletion of a T nucleotide occurring in the wild-type sequence at a position corresponding to position 101 of SEQ ID NO:19 (EXO1/rs4150021).

The biomarkers disclosed herein as being predictive of a patient's response to an immune modulating agent may also be useful in predicting a patient's response to treatment with a combination of immune modulating agents, for example, two, three, or more immune modulating agents. Accordingly, these biomarkers can be useful in determining what combinations of immune modulating agents may be effective in treating a patient's cancer.

In certain embodiments, the biomarkers disclosed herein as being predictive of a patient's response to an immune modulating agent may be useful in predicting a patient's response to treatment when the patient is progression free at six months (i.e., is progression free six months after beginning treatment with one or more immune modulating agents).

As described in the examples herein, several mutations have been identified as being pertinent to determining a cancer patient's likelihood of having a toxic response to an immune modulating agent for the treatment of cancer. These mutations (also referred to herein as "markers," "biomarkers," or "variants") are shown in SEQ ID NOS: 2, 6, 8, 11-16, and 33 of FIG. 1 as the nucleotides in square brackets.

One biomarker relevant to determining a cancer patient's likelihood of having a toxic response to an immune modulating agent is found in the human EREG gene; the marker is a SNP defined as rs1460008. In FIG. 1, 100 nucleotides upstream (5') of the mutation and 100 nucleotides downstream (3') of the mutation are shown. The mutation is a G nucleotide (variant) substituted in place of an A nucleotide (wild-type). The mutation occurs at position 101 of SEQ ID NO:11 (variant sequence) or SEQ ID NO:27 (wild-type sequence). In one embodiment, a patient identified as not carrying this mutation is identified as having a decreased likelihood of a toxic response to treatment with an immune modulating agent, whereas a patient identified as carrying the mutation is identified as having an increased likelihood of a toxic response to treatment with an immune modulating agent.

Another biomarker relevant to determining a cancer patient's likelihood of having a toxic response to an immune modulating agent is found in the human FCGR2A gene; the marker is a SNP defined as rs10919033. In FIG. 1, 100 nucleotides upstream (5') of the mutation and 100 nucleotides downstream (3') of the mutation are shown. The mutation is a C nucleotide (variant) substituted in place of an T nucleotide (wild-type). The mutation occurs at position 101 of SEQ ID NO:12 (variant sequence) or SEQ ID NO:28 (wild-type sequence). In one embodiment, a patient identified as not carrying this mutation is identified as having a decreased likelihood of a toxic response to treatment with an immune modulating agent, whereas a patient identified as carrying the mutation is identified as having an increased likelihood of a toxic response to treatment with an immune modulating agent.

Another biomarker relevant to determining a cancer patient's likelihood of having a toxic response to an immune modulating agent is also found in the human FCGR2A gene; the marker is a SNP defined as rs1801274. In FIG. 1, 100 nucleotides upstream (5') of the mutation and 100 nucleotides downstream (3') of the mutation are shown. The mutation is a C nucleotide (variant) substituted in place of an T nucleotide (wild-type). The mutation occurs at position 101 of SEQ ID NO:13 (variant sequence) or SEQ ID NO:29 (wild-type sequence). In one embodiment, a patient identified as carrying this mutation is identified as having a decreased likelihood of a toxic response to treatment with an immune modulating agent, whereas a patient identified as not carrying the mutation is identified as having an increased likelihood of a toxic response to treatment with an immune modulating agent.

Another biomarker relevant to determining a cancer patient's likelihood of having a toxic response to an immune modulating agent is found in the human IL10RB gene; the marker is a SNP defined as rs2834167. In FIG. 1, 100 nucleotides upstream (5') of the mutation and 100 nucleotides downstream (3') of the mutation are shown. The mutation is a G nucleotide (variant) substituted in place of an A nucleotide (wild-type). The mutation occurs at position 101 of SEQ ID NO:6 (variant sequence) or SEQ ID NO:22 (wild-type sequence). In one embodiment, a patient identified as carrying this mutation is identified as having a decreased likelihood of a toxic response to treatment with an immune modulating agent, whereas a patient identified as not carrying the mutation is identified as having an increased likelihood of having a toxic response to treatment with an immune modulating agent. In a further embodiment, a patient identified as carrying this mutation is identified as having an increased likelihood of a toxic response to radiation therapy. In yet a further embodiment, a patient homozygous for this mutation is identified as one having an increased likelihood of a toxic response to radiation therapy.

Another biomarker relevant to determining a cancer patient's likelihood of having a toxic response to an immune modulating agent is found in the human KRAS gene; the marker is a SNP defined as rs61764370. In FIG. 1, 100 nucleotides upstream (5') of the mutation and 100 nucleotides downstream (3') of the mutation are shown. The mutation is a G nucleotide (variant) substituted in place of a T nucleotide (wild-type). The mutation occurs at position 101 of SEQ ID NO:14 (variant sequence) or SEQ ID NO:30 (wild-type sequence). In one embodiment, a patient identified as carrying this mutation is identified as having a decreased likelihood of a toxic response to treatment with an immune modulating agent, whereas a patient identified as not carrying the mutation is identified as having an increased likelihood of a toxic response to treatment with an immune modulating agent.

Another biomarker relevant to determining a cancer patient's likelihood of having a toxic response to an immune modulating agent is found in the human miR99a promoter gene. In FIG. 1, 100 nucleotides upstream (5') of the mutation and 100 nucleotides downstream (3') of the mutation are shown. The mutation is a C nucleotide (variant) substituted in place of a T nucleotide (wild-type). The mutation occurs at position 101 of SEQ ID NO:8 (variant sequence) or SEQ ID NO:24 (wild-type sequence). In one embodiment, a patient identified as carrying this mutation is identified as having a decreased likelihood of a toxic response to treatment with an immune modulating agent, whereas a patient identified as not carrying the mutation is identified as having an increased likelihood of a toxic response to treatment with an immune modulating agent.

Another biomarker relevant to determining a cancer patient's likelihood of having a toxic response to an immune modulating agent is found in the human RAC1 gene; the marker is a SNP defined as rs9374. In FIG. 1, 100 nucleotides upstream (5') of the mutation and 100 nucleotides downstream (3') of the mutation are shown. The mutation is an A nucleotide (variant) substituted in place of a G nucleotide (wild-type). The mutation occurs at a position 101 of SEQ ID NO:15 (variant sequence) or SEQ ID NO:31 (wild-type sequence). In one embodiment, a patient identified as not carrying this mutation is identified as having a decreased likelihood of a toxic response to treatment with an immune modulating agent, whereas a patient identified as carrying the mutation is identified as having an increased likelihood of a toxic response to treatment with an immune modulating agent.

Another biomarker relevant to determining a cancer patient's likelihood of having a toxic response to an immune modulating agent is found in the human TLR4 gene; the marker is a SNP defined as rs4986790. In FIG. 1, 100 nucleotides upstream (5') of the mutation and 100 nucleotides downstream (3') of the mutation are shown. The mutation is a G nucleotide (variant) substituted in place of an A nucleotide (wild-type). The mutation occurs at position 101 of SEQ ID NO:16 (variant sequence) or SEQ ID NO:32 (wild-type sequence). In one embodiment, a patient identified as not carrying this mutation is identified as having a decreased likelihood of a toxic response to treatment with an immune modulating agent, whereas a patient identified as carrying the mutation is identified as having an increased likelihood of a toxic response to treatment with an immune modulating agent. In a further embodiment, a patient carrying this mutation is identified as having a decreased likelihood of a toxic response to radiation therapy. In yet a further embodiment, a patient identified as homozygous or heterozygous for this mutation is identified as having a decreased likelihood of a toxic response to radiation therapy.

Another biomarker relevant to determining a cancer patient's likelihood of having a toxic response to an immune modulating agent is found in the human MSH2 gene; the marker is a SNP defined as rs2303428. In FIG. 1, 100 nucleotides upstream (5') of the mutation and 100 nucleotides downstream (3') of the mutation are shown. The mutation is a C nucleotide (variant) substituted in place of a T nucleotide (wild-type). The mutation occurs at position 101 of SEQ ID NO:33 (variant sequences) or SEQ ID NO:34 (wild-type sequence). In one embodiment, a patient identified as carrying this mutation is identified as having a decreased likelihood of a toxic response to treatment with an immune modulating agent, whereas a patient identified as not carrying the mutation is identified as having an increased likelihood of a toxic response to treatment with an immune modulating agent.

Another biomarker relevant to determining a cancer patient's likelihood of having a toxic response to an immune modulating agent is found in the human CD274 gene; the marker is a SNP defined as rs4742098. In FIG. 1, 100 nucleotides upstream (5') of the mutation and 100 nucleotides downstream (3') of the mutation are shown. The mutation is a G nucleotide (variant) substituted in place of an A nucleotide (wild-type). The mutation occurs at position 101 of SEQ ID NO:2 (variant sequence) or SEQ ID NO:18 (wild-type sequence). In one embodiment, a patient identified as not carrying this mutation is identified as having an decreased likelihood of a toxic response to treatment with an immune modulating agent, whereas a patient identified as carrying the mutation is identified as having an increased likelihood of a toxic response to treatment with an immune modulating agent. In a further embodiment, a patient carrying this mutation is identified as having an increased likelihood of a toxic response to radiation therapy. In yet a further embodiment, a patient homozygous for this mutation is identified as having an increased likelihood of a toxic response to radiation therapy.

Each of the biomarkers disclosed herein as being predictive of toxicity may be used either alone or in combination with one or more of the other markers disclosed herein as predictive of toxicity in order to predict whether or not a patient will have a toxic response to an immune modulating therapy. For example, one may use one, two, three, four, five, six, seven, eight, nine, or ten of the biomarkers in determining a patient's predicted toxicity to an immune modulating therapy. In particular, determining whether a patient is homozygous or heterozygous for a particular marker associated with toxicity to an immune therapy (or does not carry the marker, i.e., the patient is wild-type) can be useful in determining the patient's predicted toxicity to an immune modulating therapy. For example, one may determine the zygosity of a patient with respect to one, two, three, four, five, six, seven, eight, nine or ten of the biomarkers disclosed herein as predictive of toxicity in order to determine the patient's predicted toxicity to an immune modulating therapy. For example, one may determine the zygosity of at least one, at least two, at least three, at least four, at least five, at least six, at least seven, at least eight, or at least nine of the aforementioned markers associated with toxicity.

For example, with respect to FCGR2A/rs10919033, if the patient is neither heterozygous nor homozygous for a C nucleotide at a position corresponding to position 101 of SEQ ID NO:12 (FCGR2A/rs10919033) (e.g., the patient is homozygous wild-type), the patient has a decreased likelihood of a toxic response to an immune modulating therapy.

With respect to TLR4/rs4986790, if the patient is neither heterozygous nor homozygous for a G nucleotide at a position corresponding to position 101 of SEQ ID NO:16 (TRL4/rs4986790) (e.g., the patient is homozygous wild-type), the patient has a decreased likelihood of a toxic response to immune modulating therapy. In a further embodiment, the patient has a decreased likelihood of a toxic response to an immune modulating therapy, if the patient is also neither heterozygous nor homozygous for a C nucleotide at a position corresponding to position 101 of SEQ ID NO:12 (FCGR2A/rs10919033).

With respect to KRAS/rs61764370, if the patient is heterozygous or homozygous for a G nucleotide at a position corresponding to position 101 of SEQ ID NO:14 (KRAS/ rs61764370) (e.g., the patient is homozygous wild-type), the patient has a decreased likelihood of a toxic response to immune modulating therapy. In a further embodiment, the patient has a decreased likelihood of a toxic response to an immune modulating therapy if the patient is also neither heterozygous nor homozygous for a C nucleotide at a position corresponding to position 101 of SEQ ID NO:12 (FCGR2A/rs10919033) and is neither heterozygous or homozygous for a G nucleotide at a position corresponding to position 101 of SEQ ID NO:16 (TRL4/rs4986790).

In one embodiment of the invention, the toxicity response of a patient to an immune modulating agent is predicted by determining the zygosity of that patient with respect to a C nucleotide at a position corresponding to position 101 of SEQ ID NO:12 (FCGR2A/rs10919033), a G nucleotide at a position corresponding to position 101 of SEQ ID NO:16 (TRL4/rs4986790), and/or a G nucleotide at a position corresponding to position 101 of SEQ ID NO:14 (KRAS/rs61764370). The zygosity of one, two, or all three of these markers may be determined and assessed to predict the patient's likely toxic response to the immune modulating agent. Alternatively, only one or only two of these markers may be assessed.

For example, in one embodiment, a patient is assessed to determine if the patient is neither heterozygous nor homozygous for a C nucleotide at a position corresponding to position 101 of SEQ ID NO:12 (FCGR2A/rs10919033). For example, in another embodiment, a patient is assessed to determine if the patient is neither heterozygous nor homozygous for a G nucleotide at a position corresponding to position 101 of SEQ ID NO:16 (TRL4/rs4986790). For example, in another embodiment, a patient is assessed to determine if the patient is heterozygous or homozygous for a G nucleotide at a position corresponding to position 101 of SEQ ID NO:14 (KRAS/rs61764370).

In one embodiment of the invention, determining whether a patient is likely to have a toxic or non-toxic response to an immune modulating agent, it is determined whether the patient carries or does not carry one or more of the following mutations:
 a) a G nucleotide at a position corresponding to position 101 of SEQ ID NO:11 (EREG/rs1460008);
 b) a C nucleotide at a position corresponding to position 101 of SEQ ID NO:12 (FCGR2A/rs10919033);
 c) a C nucleotide at a position corresponding to position 101 of SEQ ID NO:13 (FCGR2A/rs1801274);
 d) a G nucleotide at a position corresponding to position 101 of SEQ ID NO:6 (IL10RB/rs2834167);
 e) a G nucleotide at a position corresponding to position 101 of SEQ ID NO:14 (KRAS/rs61764370);
 f) a C nucleotide at a position corresponding to position 101 of SEQ ID NO:8 (miR99a promoter);
 g) an A nucleotide at a position corresponding to position 101 of SEQ ID NO:15 (RAC1/rs9374);
 h) a G nucleotide at a position corresponding to position 101 of SEQ ID NO:16 (TRL4/rs4986790);
 i) a G nucleotide at a position corresponding to position 101 of SEQ ID NO:2 (CD274/rs4742098); and
 j) a C nucleotide at a position corresponding to position 101 of SEQ ID NO:33 (MSH2/rs2303428).

The assessment of the patient's likelihood of a toxic response to an immune modulating agent may be based on determining the presence or absence of only one, only two, only three, only four, only five, only six, only seven, only eight, only nine or all ten of these markers, but does not necessarily require assessment of all ten markers. For example, the assessment may be based on determining the presence of absence of at least one, at least two, at least three, at least four, at least five, at least six, at least seven, at least eight, or at least nine of the aforementioned markers associated with toxicity.

When the immune modulating agent is an anti-PD1 or anti-PDL1 antibody therapy, a particular subset of biomarkers has been determined as being relevant to determining if a patient will have a toxic response to the antibody therapy. In particular, if a patient is identified as not carrying one or more of the following mutations, the patient will be considered to have a decreased risk of a toxic response to the antibody therapy:
 a) a G nucleotide at a position corresponding to position 101 of SEQ ID NO:11 (EREG/rs1460008);
 b) a C nucleotide at a position corresponding to position 101 of SEQ ID NO:12 (FCGR2A/rs10919033);
 c) an A nucleotide at a position corresponding to position 101 of SEQ ID NO:15 (RAC1/rs9374);
 d) a G nucleotide at a position corresponding to position 101 of SEQ ID NO:16 (TRL4/rs4986790); or
 e) a G nucleotide at a position corresponding to position 101 of SEQ ID NO:2 (CD274/rs4742098).

If the patient does not carry one or more of these mutations, the patient is predicted as having an decreased probability of having a toxic response to the agent. In one embodiment, it is determined whether the patient carries one, two, three, four or all five of the aforementioned biomarkers. For example, the determination of whether a patient has a decreased probability of a toxic response to the agent may be based on whether the patient does not carry only one, only two, only three, only four, or all five biomarkers, but may not require assessment of all five markers. For example, the assessment may be based on determining the presence of absence of at least one, at least two, at least three, or at least four of the aforementioned markers associated with toxicity.

When the immune modulating agent is an anti-PD1 or anti-PDL1 antibody therapy, a particular subset of biomarkers has been determined as being relevant to determining if a patient will have a toxic response to the antibody therapy. In particular, if a patient is identified as carrying one or more of the following mutations, the patient will be considered to have a decreased risk of a toxic response to the antibody therapy:
 a) a C nucleotide at a position corresponding to position 101 of SEQ ID NO:13 (FCGR2A/rs1801274);
 b) a G nucleotide at a position corresponding to position 101 of SEQ ID NO:6 (IL10RB/rs2834167);
 c) a G nucleotide at a position corresponding to position 101 of SEQ ID NO:14 (KRAS/rs61764370);
 d) a C nucleotide at a position corresponding to position 101 of SEQ ID NO:8 (miR99a promoter); or
 e) a C nucleotide at a position corresponding to position 101 of SEQ ID NO:33 (MSH2/rs2303428).

If the patient does carries one or more of these mutations, the patient is predicted as having a decreased probability of having a toxic response to the agent. In one embodiment, it is determined whether the patient carries one, two, three, four, or all five of the aforementioned biomarkers. For example, the determination of whether a patient has a decreased probability of a toxic response to the agent may be based on whether the patient carries only one, only two, only three, only four, or all five biomarkers, but may not require assessment of all four markers. For example, the assessment may be based on determining the presence of absence of at least one, at least two, at least three, or at least four of the aforementioned markers associated with toxicity.

When the immune modulating agent is radiation therapy, a particular subset of biomarkers has been determined to be relevant to determining if a patient will have a toxic response to radiation therapy.

One biomarker relevant to determining whether a cancer patient will have a toxic response to radiation therapy is found in the human CD274 gene; the marker is a SNP defined as rs4742098. In FIG. 1, 100 nucleotides upstream (5') of the mutation and 100 nucleotides downstream (3') of the mutation are shown. The mutation is a G nucleotide (variant) substituted in place of an A nucleotide (wild-type). The mutation occurs at position 101 of SEQ ID NO:2 (variant sequence) or SEQ ID NO:18 (wild-type sequence). In one embodiment, a patient identified as not carrying this mutation or as heterozygous for this mutation is identified as having an increased likelihood of a non-toxic response to radiation therapy, whereas a patient identified as being homozygous for this mutation is identified as having an increased risk for a toxic response to radiation therapy.

Another biomarker relevant to determining whether a cancer patient will have a toxic response to radiation therapy is found in the human IL10RB gene; the marker is a SNP defined as rs2834167. In FIG. 1, 100 nucleotides upstream (5') of the mutation and 100 nucleotides downstream (3') of the mutation are shown. The mutation is a G nucleotide (variant) substituted in place of an A nucleotide (wild-type). The mutation occurs at position 101 of SEQ ID NO:6 (variant sequence) or SEQ ID NO:22 (wild-type sequence). In one embodiment, a patient identified as not carrying this mutation or as heterozygous for this mutation is identified as having an increased likelihood of a non-toxic response to radiation therapy, whereas a patient identified as being homozygous for this mutation is identified as having an increased risk for a toxic response to radiation therapy.

Another biomarker relevant to determining whether a cancer patient will have a toxic response to radiation therapy is found in the human TRL4 gene; the marker is a SNP defined as rs4986790. In FIG. 1, 100 nucleotides upstream (5') of the mutation and 100 nucleotides downstream (3') of the mutation are shown. The mutation is a G nucleotide (variant) substituted in place of an A nucleotide (wild-type). The mutation occurs at position 101 of SEQ ID NO:16 (variant sequence) or SEQ ID NO:32 (wild-type sequence). In one embodiment, a patient identified as carrying this mutation (whether heterozygous or homozygous) is identified as having an increased likelihood of a non-toxic response to radiation therapy, whereas a patient identified as not carrying the mutation is identified as having an increased likelihood of having a toxic response to treatment with an immune modulating agent.

In one embodiment, in order to determine if a patient will have a toxic response to radiation therapy, it is determined whether the patient carries one or more of the following markers:
  a) a G nucleotide at a position corresponding to position 101 of SEQ ID NO16 (TRL4/rs4986790);
  b) a G nucleotide at a position corresponding to position 101 of SEQ ID NO:2 (CD274/rs4742098); and/or
  c) a G nucleotide at a position corresponding to position 101 of SEQ ID NO:6 (IL10RB/rs2834167).

In one embodiment, if the patient carries a G nucleotide at a position corresponding to position 101 of SEQ ID NO:16 (TRL4/rs4986790), the patient will have a decreased risk of toxic response to radiation therapy. In another embodiment, if the patient carries a G nucleotide at a position corresponding to position 101 of SEQ ID NO:2 (CD274/rs4742098), the patient will have an increased risk of toxic response to radiation therapy. In yet another embodiment, if the patient carries a G nucleotide at a position corresponding to position 101 of SEQ ID NO:6 (IL10RB/rs2834167), the patient will have an increased risk of toxic response to radiation therapy.

In a further embodiment, in order to determine the risk of a toxic response by a patient to radiation therapy, the zygosity of the patient with respect to certain biomarkers is determines. For example, in one embodiment, if the patient is heterozygous or homozygous for a G nucleotide at a position corresponding to position 101 of SEQ ID NO:16 (TRL4/rs4986790), the patient has a decreased risk for a toxic response to radiation therapy. In another embodiment, if the patient is not homozygous for a G nucleotide at a position corresponding to position 101 of SEQ ID NO:2 (CD274/rs4742098), the patient has a decreased risk for a toxic response to radiation therapy. In yet another embodiment, if the patient is not homozygous for a G nucleotide at a position corresponding to position 101 of SEQ ID NO:6 (IL10RB/rs2834167), the patient has a decreased risk for a toxic response to radiation therapy.

Definitions

As used herein, the terms "response" or "responding" in the context of a patient's response to a therapy or treatment for cancer refer to the RECIST (Response Evaluation Criteria in Solid Tumors) criteria for evaluating response of target lesions to a cancer therapy. According to the RECIST criteria, patients who respond are categorized as either "complete responders" (disappearance of all target lesions) or "partial responders" (at least a 30% decrease in the sum of the longest diameter of target lesions, taking a reference the baseline sum longest diameter); non-responders are placed into one of two categories: stable disease (neither sufficient shrinkage to qualify for partial response nor sufficient increase to qualify for progressive disease, taking as reference the smallest sum longest diameter since start of treatment) or progressive disease (at least a 20% increase in the sum of the longest diameter of target lesions, taking as reference the smallest sum longest diameter recorded since treatment started or the appearance of one or more new lesions). The RECIST criteria is discussed in detail in, e.g., Eisenhauer et al., *Eur. J. Cancer,* 2009: 25:228-247. Accordingly, as described herein, responding to therapy refers to patients falling within the RECIST categories of complete or partial responder, whereas as not responding refers to patients falling within the RECIST categories of stable disease or progressive disease.

As used herein, the terms "treat," "treating," or "treatment" in the context of cancer refer to (a) slowing of growth of a tumor, (b) cessation of growth of a tumor, (c) regression, or (d) improvement in one or more the patient's symptoms. According to one embodiment of the invention, "treating" or "treat" may refer to patient outcomes where a patient receiving an immune modulating therapy exhibits a response to that therapy.

As used herein, the term "toxicity" or "toxic response" refers to the occurrence of one or more immune response adverse reaction(s) (irAEs), a particular class of adverse reactions a patient may experience in response to a cancer therapy, and most commonly cancer immunotherapy. irAEs are believed to occur as a result of stimulation of the immune system by the cancer therapy and include different forms of auto-immunity induced by the administration of these therapies, such as, for example, pneumonitis, hepatitis, pancreatitis, and colitis. For example, irAEs are particularly observed in patients who are treated with checkpoint inhibitor therapies. irAEs are more fully discussed in, for example, Abdel-Wahab et al., PLOS ONE, 11 (7):e0160221 (2016). The toxicity of irAEs is commonly graded on a scale of 0-5, with 0 representing no adverse event or an event within normal limits, 1 representing a mild adverse event, 2 representing a moderate adverse event, 3 representing a severe and undesirable adverse event, 4 representing a life threatening or disabling adverse event, and 5 representing a death related to an adverse event. A "toxic response" or "high toxicity" as referred to herein therefore refers to irAEs of grade 2 or higher on this scale, whereas grades or 0 or 1 are considered "non-toxic responses" or "low toxicity."

The term "increased probability/likelihood" or "reduced probability/likelihood" in the context of the present invention, relates to the increased or reduced probability that an event will occur over a specific time period, and can mean a subject's "absolute" probability or "relative" probability. Absolute probability can be measured with reference to either actual observation post-measurement for the relevant time cohort, or with reference to index values developed from statistically valid historical cohorts that have been followed for the relevant time period. Relative probability refers to the ratio of absolute probabilities of a subject compared either to the absolute probabilities of low probability cohorts or an average population probability, which can vary by how clinical probabilities are assessed. Odds ratios, the proportion of positive events to negative events for a given test result, are also commonly used (odds are according to the formula $p/(1-p)$ where p is the probability of event and $(1-p)$ is the probability of no event) to no-conversion.

A patient's "increased likelihood or probability" of response to a therapy may be based on a comparison to the rate of response (or predicted rate of response) of a cohort of patients having a different genotype than the patient's genotype with respect to a particular biomarker or biomarkers. An "increased likelihood or probability" of response to a therapy may also be based on a comparison to the rate of response (or predicted rate of response) for a cohort of patients without taking the marker (or markers) into consideration.

A patient's "decreased likelihood or probability" of response to a therapy may be based on a comparison to the rate of response (or predicted rate of response) of a cohort of patients having a different genotype than the patient's genotype with respect to a particular biomarker or biomarkers. A "decreased likelihood or probability" of response to a therapy may also be based on a comparison to the rate of response (or predicted rate of response) for a cohort of patients without taking the marker (or markers) into consideration.

A patient's "increased likelihood or probability" of having a toxic response to a therapy may be based on a comparison to the rate of toxic response (or predicted rate of toxic response) of a cohort of patients having a different genotype than the patient's genotype with respect to a particular biomarker or biomarkers. An "increased likelihood or probability" of having a toxic response to a therapy may also be based on a comparison to the rate of toxic response (or predicted rate of response) for a cohort of patients without taking the marker (or markers) into consideration.

A patient's "decreased likelihood or probability" of having a toxic response to a therapy may be based on a comparison to the rate of toxic response (or predicted rate of toxic response) of a cohort of patients having a different genotype than the patient's genotype with respect to a particular biomarker or biomarkers. A "decreased likelihood or probability" of having a toxic response to a therapy may also be based on a comparison to the rate of toxic response (or predicted rate of response) for a cohort of patients without taking the marker (or markers) into consideration.

The biomarkers disclosed herein as being predictive of a patient's toxicity to an immune modulating agent may also be useful in predicting a patient's toxicity to treatment with a combination of immune modulating agents, for example, two, three, or more immune modulating agents. Accordingly, these biomarkers can be useful in determining what combinations of immune modulating agents may be used without having a toxic response in a patient.

Immune Modulating Agents

The mutations described herein are relevant biomarkers for determining the therapeutic response of a cancer patient to treatment with an immune modulating agent or for determining whether a patient will have a toxic response to treatment with an immune modulating agent. In one embodiment, the immune modulating agent is designed to enhance the immune system of the patient. Immune modulating agents that function to initially stimulate a weakened immune system are preferred over agents which rely on a fully functional immune system for their benefit. Immune modulating agents may include antibodies, cytokines, adoptive cell transfer, anti-cancer vaccines, checkpoint inhibitors or non-biologic drugs that stimulate the immune system. The terms "immune modulating agent" and "immune modulating therapy" are used synonymously herein.

The immune modulating agent may be an anti-cancer antibody such as cetuximab, panitumumab, nimotuzumumab, matuzumab, futuximab, imgatuzumab, necitumumab, alemtuzumab, trastuzumab, ibritumomab, brentuximab, blinatumomab, bevacizumab, cetuximab, or ipilimumab. The immune modulating agent may be an anti-cancer antibody conjugated to a drug. For example, the immune modulating agent may be ibritumomab tiuxetan, brentuximab vedotin, ado-trastuzumab emtansine, or denileukin diftitox. The immune modulating agent may be a cytokine such as IL-2, IL-12, IL-21, IFN-α, IFN-β, or IFN-γ. The cytokine may be conjugated to an antibody. The immune modulating agent may also be a drug that stimulates the immune system such as thalidomide, lanlidomide, pomalidomide or imiquimod.

The immune modulating agent may be radiation. The radiation may be external-beam radiation therapy such as photon beams of x-rays or gamma rays, electron beams, or proton therapy. The radiation may be internal radiation therapy (brachytherapy) where radiation is delivered from a radiation source placed inside or on the body, even inside the tumor tissue. The radiation source may be a radioactive isotope in the form of a seed or pellet implanted in or placed on the patient. The radiation may be systemic radiation therapy administered orally or by injection. The radioactive substance may be radioactive iodine ($^{131}$I), or an antibody conjugated to a radioactive substance such as ibritumomab tiuxetan or I131-tositumomab.

In another embodiment, the immune modulating agent may be a checkpoint inhibitor. For example, in one embodiment, the immune modulating agent is an anti-PD1 or anti-PDL1 antibody. According to one aspect of the invention, the patients treated according to the methods of the invention are treated with an anti-PDL1 or anti-PD1 therapy. In one embodiment, the therapy is an anti-PDL1 antibody. In another embodiment, the therapy is an anti-PD1 antibody. In one embodiment, the anti-PD1 antibody is Opdivo® (nivolumab) or Keytruda® (pembrolizumab). In another embodiment, the anti-PDL1 antibody is BMS-936559 (MDX-1105), Tecentriq® (atezolizumab), Imfinzi® (durvalumab), or Bavencio® (avelumab). In other embodiments, the anti-PD1 antibody is an antibody capable of binding to PD1. In yet other embodiments, the anti-PDL1 antibody is an antibody capable of binding to PDL1. In another embodiment, the immune modulating agent may be an anti-CTLA4 antibody. For example, in one embodiment, the immune modulating agent is ipilimumab.

In another embodiment, the immune modulating agent may be a cellular based therapy effected through an adoptive cell transfer. For example, the immune modulating agent may be a chimeric antigen receptor T cells (CAR-T cells).

In yet another embodiment, the immune modulating agent may be an anti-cancer vaccine. For example, in one embodiment, the immune modulating agent may be a dendritic cell vaccine.

As used herein, the term "antibody" means an intact antibody (e.g., an intact monoclonal antibody). In some embodiments, an "antibody" includes an antigen-binding fragment of an antibody. Antigen-binding fragments include Fab, Fab', F(ab')2, Fv, single chain antibodies (e.g., scFv), minibodies, diabodies, and single-domain antibodies ("sdAb" or "nanobodies" or "camelids"). In yet other embodiments, an antibody includes an intact antibody or antigen-binding fragment of an antibody (e.g., a phage display antibody including a fully human antibody, a semi-synthetic antibody or a fully synthetic antibody) that has been optimized, engineered or chemically conjugated. Examples of antibodies that have been optimized are affinity-matured antibodies. Examples of antibodies that have been engineered are Fc optimized antibodies, and multispecific antibodies (e.g., bispecific antibodies). An antibody conjugated to a toxin moiety is an example of a chemically conjugated antibody.

Methods for producing antibodies, such as anti-PDL1 and anti-PD1 antibodies or other anti-cancer antibodies, are known in the art. For example, DNA molecules encoding light chain variable regions and heavy chain variable regions can be chemically synthesized. Synthetic DNA molecules can be ligated to other appropriate nucleotide sequences, including, e.g., constant region coding sequences, and expression control sequences, to produce conventional gene expression constructs encoding the desired antibodies. Production of defined gene constructs is within routine skill in the art. Alternatively, the sequences provided herein can be cloned out of hybridomas by conventional hybridization techniques or polymerase chain reaction (PCR) techniques, using synthetic nucleic acid probes whose sequences are based on known sequences regarding genes encoding the heavy and light chains of murine antibodies in hybridoma cells.

Nucleic acids encoding the antibodies disclosed herein can be incorporated (ligated) into expression vectors, which can be introduced into host cells through conventional transfection or transformation techniques. Exemplary host cells are E. coli cells, Chinese hamster ovary (CHO) cells, HeLa cells, baby hamster kidney (BHK) cells, monkey kidney cells (COS), human hepatocellular carcinoma cells (e.g., Hep G2), and myeloma cells that do not otherwise produce IgG protein. Transformed host cells can be grown under conditions that permit the host cells to express the genes that encode the immunoglobulin light and/or heavy chain variable regions.

Specific expression and purification conditions will vary depending upon the expression system employed. For example, if a gene is to be expressed in E. coli, it is first cloned into an expression vector by positioning the engineered gene downstream from a suitable bacterial promoter, e.g., Trp or Tac, and a prokaryotic signal sequence. The expressed secreted protein accumulates in refractile or inclusion bodies, and can be harvested after disruption of the cells by French press or sonication. The refractile bodies then are solubilized, and the proteins refolded and cleaved by methods known in the art.

If a DNA construct encoding an antibody disclosed herein is to be expressed in eukaryotic host cells, e.g., CHO cells, it is first inserted into an expression vector containing a suitable eukaryotic promoter, a secretion signal, IgG enhancers, and various introns. This expression vector optionally contains sequences encoding all or part of a constant region, enabling an entire, or a part of, a heavy and/or light chain to be expressed. In some embodiments, a single expression vector contains both heavy and light chain variable regions to be expressed.

The gene construct can be introduced into eukaryotic host cells using conventional techniques. The host cells express variable light chain (VL) or variable heavy chain (VH) fragments, VL-VH heterodimers, VH-VL or VL-VH single chain polypeptides, complete heavy or light immunoglobulin chains, or portions thereof, each of which may be attached to a moiety having another function (e.g., cytotoxicity). In some embodiments, a host cell is transfected with a single vector expressing a polypeptide expressing an entire, or part of, a heavy chain (e.g., a heavy chain variable region) or a light chain (e.g., a light chain variable region). In other embodiments, a host cell is transfected with a single vector encoding (a) a polypeptide comprising a heavy chain variable region and a polypeptide comprising a light chain variable region, or (b) an entire immunoglobulin heavy chain and an entire immunoglobulin light chain. In still other embodiments, a host cell is co-transfected with more than one expression vector (e.g., one expression vector expressing a polypeptide comprising an entire, or part of, a heavy chain or heavy chain variable region, and another expression vector expressing a polypeptide comprising an entire, or part of, a light chain or light chain variable region).

A method of producing a polypeptide comprising an immunoglobulin heavy chain variable region or a polypeptide comprising an immunoglobulin light chain variable region may comprise growing a host cell transfected with an expression vector under conditions that permits expression of the polypeptide comprising the immunoglobulin heavy chain variable region or the polypeptide comprising the immunoglobulin light chain variable region. The polypeptide comprising a heavy chain variable region or the polypeptide comprising the light chain variable region then may be purified using techniques well known in the art, e.g., affinity tags such as glutathione-S-transferase (GST) and histidine tags.

Human monoclonal antibodies can be isolated or selected from phage display libraries including immune, naïve and synthetic libraries. Antibody phage display libraries are known in the art, see, e.g., Hoet et al., NATURE BIOTECH. 23:344-348, 2005; Soderlind et al., NATURE BIOTECH. 18:852-856, 2000; Rothe et al., J. MOL. BIOL. 376:1182-1200, 2008; Knappik et al., J. MOL. BIOL. 296:57-86, 2000; and Krebs et al., J. IMMUNOL. METH. 254:67-84, 2001. When used as a therapeutic, human antibodies isolated by phage display may be optimized (e.g., affinity-matured) to improve biochemical characteristics including affinity and/or specificity, improve biophysical properties including aggregation, stability, precipitation and/or non-specific interactions, and/or to reduce immunogenicity. Affinity-maturation procedures are within ordinary skill in the art. For example, diversity can be introduced into an immunoglobulin heavy chain and/or an immunoglobulin light chain by DNA shuffling, chain shuffling, CDR shuffling, random mutagenesis and/or site-specific mutagenesis.

In some embodiments, isolated human antibodies contain one or more somatic mutations. In these cases, antibodies can be modified to a human germline sequence to optimize the antibody (i.e., a process referred to as germlining).

Generally, an optimized antibody has at least the same, or substantially the same, affinity for the antigen as the non-optimized (or parental) antibody from which it was derived. Preferably, an optimized antibody has a higher affinity for the antigen when compared to the parental antibody.

Human antibody fragments (e.g., parental and optimized variants) can be engineered to contain certain constant (i.e., Fc) regions with a specified effector function (e.g., antibody-dependent cellular cytotoxicity (ADCC)). Human constant regions are known in the art.

The antibody can be conjugated to an effector moiety such as a small molecule toxin or a radionuclide using standard in vitro conjugation chemistries. If the effector moiety is a polypeptide, the antibody can be chemically conjugated to the effector or joined to the effector as a fusion protein. Construction of fusion proteins is within ordinary skill in the art.

Methods for reducing or eliminating the antigenicity of antibodies and antibody fragments are known in the art. When the antibodies are to be administered to a human, the antibodies preferably are "humanized" to reduce or eliminate antigenicity in humans. Preferably, a humanized antibody has the same or substantially the same affinity for the antigen as the non-humanized mouse antibody from which it was derived.

In one humanization approach, chimeric proteins are created in which mouse immunoglobulin constant regions are replaced with human immunoglobulin constant regions. See, e.g., Morrison et al., 1984, Proc. Nat. Acad. Sci. 81:6851-6855, Neuberger et al., 1984, Nature 312:604-608; U.S. Pat. No. 6,893,625 (Robinson); U.S. Pat. No. 5,500,362 (Robinson); and U.S. Pat. No. 4,816,567 (Cabilly).

In an approach known as CDR grafting, the CDRs of the light and heavy chain variable regions are grafted into frameworks from another species. For example, murine CDRs can be grafted into human FRs. In some embodiments, the CDRs of the light and heavy chain variable regions of an anti-ErbB3 antibody are grafted onto human FRs or consensus human FRs. To create consensus human FRs, FRs from several human heavy chain or light chain amino acid sequences are aligned to identify a consensus amino acid sequence. CDR grafting is described in U.S. Pat. No. 7,022,500 (Queen); U.S. Pat. No. 6,982,321 (Winter); U.S. Pat. No. 6,180,370 (Queen); U.S. Pat. No. 6,054,297 (Carter); U.S. Pat. No. 5,693,762 (Queen); U.S. Pat. No. 5,859,205 (Adair); U.S. Pat. No. 5,693,761 (Queen); U.S. Pat. No. 5,565,332 (Hoogenboom); U.S. Pat. No. 5,585,089 (Queen); U.S. Pat. No. 5,530,101 (Queen); Jones et al. (1986) Nature 321: 522-525; Riechmann et al. (1988) Nature 332: 323-327; Verhoeyen et al. (1988) Science 239: 1534-1536; and Winter (1998) Febs Lett 430: 92-94.

In an approach called "SUPERHUMANIZATION™," human CDR sequences are chosen from human germline genes, based on the structural similarity of the human CDRs to those of the mouse antibody to be humanized. See, e.g., U.S. Pat. No. 6,881,557 (Foote); and Tan et al., 2002, J. Immunol 169:1119-1125.

Other methods to reduce immunogenicity include "reshaping," "hyperchimerization," and "veneering/resurfacing." See, e.g., Vaswami et al., 1998, Annals of Allergy, Asthma, & Immunol. 81:105; Roguska et al., 1996, Prot. Engineer 9:895-904; and U.S. Pat. No. 6,072,035 (Hardman). In the veneering/resurfacing approach, the surface accessible amino acid residues in the murine antibody are replaced by amino acid residues more frequently found at the same positions in a human antibody. This type of antibody resurfacing is described, e.g., in U.S. Pat. No. 5,639,641 (Pedersen).

Another approach for converting a mouse antibody into a form suitable for medical use in humans is known as ACTIVMAB™ technology (Vaccinex, Inc., Rochester, NY), which involves a vaccinia virus-based vector to express antibodies in mammalian cells. High levels of combinatorial diversity of IgG heavy and light chains are said to be produced. See, e.g., U.S. Pat. No. 6,706,477 (Zauderer); U.S. Pat. No. 6,800,442 (Zauderer); and U.S. Pat. No. 6,872,518 (Zauderer).

Another approach for converting a mouse antibody into a form suitable for use in humans is technology practiced commercially by KaloBios Pharmaceuticals, Inc. (Palo Alto, CA). This technology involves the use of a proprietary human "acceptor" library to produce an "epitope focused" library for antibody selection.

Another approach for modifying a mouse antibody into a form suitable for medical use in humans is HUMAN ENGINEERING™ technology, which is practiced commercially by XOMA (US) LLC. See, e.g., PCT Publication No. WO 93/11794 and U.S. Pat. Nos. 5,766,886; 5,770,196; 5,821,123; and 5,869,619.

Any suitable approach, including any of the above approaches, can be used to reduce or eliminate human immunogenicity of an antibody disclosed herein.

Methods of making multispecific antibodies are known in the art. Multi-specific antibodies include bispecific antibodies. Bispecific antibodies are antibodies that have binding specificities for at least two different epitopes. Exemplary bispecific antibodies bind to two different epitopes of the antigen of interest. Bispecific antibodies can be prepared as full length antibodies or antibody fragments (e.g., F(ab')$_2$ bispecific antibodies and diabodies) as described, for example, in Milstein et al., Nature 305:537-539 (1983), WO 93/08829, Traunecker et al., EMBO J., 10:3655-3659 (1991), WO 94/04690, Suresh et al., Methods in Enzymology, 121:210 (1986), WO96/27011, Brennan et al., Science, 229: 81 (1985), Shalaby et al., J. Exp. Med., 175: 217-225 (1992), Kostelny et al., J. Immunol., 148(5):1547-1553 (1992), Hollinger et al., PNAS, 90:6444-6448, Gruber et al., J. Immunol., 152:5368 (1994), Wu et al., Nat. Biotechnol., 25(11): 1290-1297, U.S. Patent Publication No. 2007/0071675, and Bostrom et al., Science 323:1640-1644 (2009).

SNP Genotyping Methods

The process of determining which specific nucleotide (i.e., allele) is present at each of one or more SNP positions is referred to as SNP genotyping. The present invention provides methods of SNP genotyping in order to determine whether a patient has a particular genotype with respect to the mutations disclosed herein as useful biomarkers in predicting a patient's therapeutic and toxicity response to immune modulating agents.

Nucleic acid samples can be genotyped to determine which allele(s) is/are present at any given genetic region (e.g., SNP position) of interest by methods well known in the art. The neighboring sequence can be used to design SNP detection reagents such as oligonucleotide probes, which may optionally be implemented in a kit format. Exemplary SNP genotyping methods are described in Chen et al. (2003) PHARMACOGENOMICS J. 3(2):77-96; Kwok et al. (2003) CURR ISSUES MOL. BIOL. 5(2):43-60; Shi (2002) AM J PHARMACOGENOMICS 2(3):197-205; and Kwok (2001) ANNU REV GENOMICS HUM GENET 2:235-58. Exemplary techniques for high-throughput SNP genotyping are described in Marnellos (2003) CURR OPIN DRUG DISCOV DEVEL. 6(3):317-21. Common SNP genotyping methods include, but are not limited to, quantitative PCR, TaqMan assays, molecular beacon assays, nucleic acid arrays, allele-specific primer extension, allele-specific PCR, arrayed primer extension, homogeneous primer extension assays, primer extension with detection by mass spectrometry, pyrosequencing, multiplex primer extension sorted on genetic arrays, ligation with rolling circle amplification, homogeneous ligation, OLA (U.S. Pat. No. 4,988,167), multiplex ligation reaction sorted on genetic arrays, restriction-fragment length polymorphism, single base extension-tag assays, and the Invader assay. Such methods may be used in combination with detection mechanisms such as, for example, luminescence or chemiluminescence detection, fluorescence detection, time-resolved fluorescence detection, fluorescence resonance energy transfer, fluorescence polarization, mass spectrometry, and electrical detection. These methods are well known in the art.

A biological sample for determination of the presence or absence of any of the mutations disclosed herein can be any tissue or fluid from the patient that contains nucleic acids. Various embodiments include paraffin imbedded tissue, frozen tissue, surgical fine needle aspirations, and cells of various tissues of the subject, such as blood cells or a cheek swab.

In one embodiment, determining whether a patient is a carrier of a particular germ-line mutation, or has a particular genotype or zygosity with respect to that mutation, is based on genetically evaluating normal cells (as opposed to tumor cells) from the patient, for example, blood cells or cells from a cheek swab.

Administration of Immune Modulating Agents

Immune modulating agents of the invention may be administered to patients in a therapeutically effective amount. If the immune modulating agent is radiation, the radiation may be administered through external beam radiation therapy (e.g., photon beams such as x-rays or gamma rays, proton therapy, electron therapy) or stereotactic body radiation therapy (SBRT) or by brachytherapy, i.e., internally placed radioactive material. The radiation may be also be administered systemically, for example, by mouth or by injection into a vein. A therapeutically effective amount of external beam therapy or SBRT may be in the range of 20-80 Gy/Kg or 40-70 Gy/Kg or 60-80 Gy/Kg. A therapeutically effective amount of brachytherapy may deliver a dose of up to 150 Gy over several months or 60 Gy in 7 days.

Generally, a therapeutically effective amount of the agent, such as an antibody or non-biologic drug is in the range of 0.1 mg/kg to 100 mg/kg, e.g., 1 mg/kg to 100 mg/kg, e.g., 1 mg/kg to 10 mg/kg. The amount administered will depend on variables such as the type and extent of disease or indication to be treated, the overall health of the patient, the in vivo potency of the agent, the pharmaceutical formulation, and the route of administration. The initial dosage can be increased beyond the upper level in order to rapidly achieve the desired blood-level or tissue level. Alternatively, the initial dosage can be smaller than the optimum, and the dosage may be progressively increased during the course of treatment. The optimal dose can be determined by routine experimentation. For parenteral administration a dose between 0.1 mg/kg and 100 mg/kg, alternatively between 0.5 mg/kg and 50 mg/kg, alternatively, between 1 mg/kg and 25 mg/kg, alternatively between 2 mg/kg and 10 mg/kg, alternatively between 5 mg/kg and 10 mg/kg is administered and may be given, for example, once weekly, once every other week, once every third week, or once monthly per treatment cycle. In one embodiment, the dose is 200 mg every 3 weeks via intravenous administration, whereas in another embodiment, the dose is 2 mg/kg every 3 weeks via intravenous administration. In another embodiment, the dose is 240 mg every 2 weeks via intravenous administration, while in yet another embodiment, the dose is or 3 mg/kg every 2 weeks via intravenous administration. In yet another embodiment, the dose is 1200 mg every 3 weeks via intravenous administration.

For therapeutic use, immune modulating agents of the invention are preferably combined with a pharmaceutically acceptable carrier. As used herein, "pharmaceutically acceptable carrier" means buffers, carriers, and excipients suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

Pharmaceutical compositions containing immune modulating agents can be presented in a dosage unit form and can be prepared by any suitable method. A pharmaceutical composition should be formulated to be compatible with its intended route of administration. Examples of routes of administration are intravenous (IV), intradermal, inhalation, transdermal, topical, transmucosal, and rectal administration. The pharmaceutical compositions are intended for parenteral, intranasal, topical, oral, or local administration, such as by a transdermal means, for therapeutic treatment. The pharmaceutical compositions can be administered parenterally (e.g., by intravenous, intramuscular, or subcutaneous injection), or by oral ingestion, or by topical application or intraarticular injection at areas affected by the vascular or cancer condition. Additional routes of administration include intravascular, intra-arterial, intratumor, intraperitoneal, intraventricular, intraepidural, as well as nasal, ophthalmic, intrascleral, intraorbital, rectal, topical, or aerosol inhalation administration.

The invention provides compositions for parenteral administration that comprise the above mention agents dissolved or suspended in an acceptable carrier, preferably an aqueous carrier, e.g., water, buffered water, saline, PBS, and the like. The compositions may contain pharmaceutically acceptable auxiliary substances as required to approximate physiological conditions, such as pH adjusting and buffering agents, tonicity adjusting agents, wetting agents, detergents and the like. The invention also provides compositions for oral delivery, which may contain inert ingredients such as binders or fillers for the formulation of a tablet, a capsule, and the like. Furthermore, this invention provides compositions for local administration, which may contain inert ingredients such as solvents or emulsifiers for the formulation of a cream, an ointment, and the like.

A preferred route of administration for antibodies is IV infusion. Useful formulations can be prepared by methods well known in the pharmaceutical art. For example, see Remington's Pharmaceutical Sciences, 18th ed. (Mack Publishing Company, 1990). Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor ELTM (BASF, Parsippany, NJ) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyethylene glycol), and suitable mixtures thereof.

Pharmaceutical formulations preferably are sterile. Sterilization can be accomplished, for example, by filtration through sterile filtration membranes. Where the composition is lyophilized, filter sterilization can be conducted prior to or following lyophilization and reconstitution. Aqueous solutions may be packaged for use as-is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above-mentioned agent or agents, such as in a sealed package of tablets or capsules.

In one embodiment, the pharmaceutical carrier for the antibody formulation may include, for example, mannitol, penetetic acid, polysorbate 80, sodium chloride, sodium citrate dehydrate and sterile water. An acid such as hydrochloric acid and/or sodium hydroxide may be added as necessary to adjust the pH of the formulation. In one embodiment, the antibody is formulated in a liquid solution where each 1 mL contains mannitol (30 mg), pentetic acid (0.008 mg), polysorbate 80 (0.2 mg), sodium chloride (2.92 mg), sodium citrate dihydrate (5.88 mg), and sterile water for injection (USP). In one particular embodiment, the antibody is nivolumab and is contained in a liquid formulation where each 1 mL of solution contains nivolumab (10 mg), mannitol (30 mg), pentetic acid (0.008 mg), polysorbate 80 (0.2 mg), sodium chloride (2.92 mg), sodium citrate dihydrate (5.88 mg), and sterile water for injection (USP) as well as hydrochloric acid and/or sodium hydroxide to adjust pH to 6, if needed.

In another embodiment, the pharmaceutical carrier for the antibody formulation may include, for example L-histidine, polysorbate, and sucrose. An acid such as hydrochloric acid or sodium hydroxide may be added as necessary to adjust the pH of the formulation. In one particular embodiment, the antibody is formulated in a liquid solution where each 1 mL of solution contains L-histidine (1.55 mg), polysorbate 80 (0.2 mg), sucrose (70 mg), and sterile Water for Injection, USP. In one particular embodiment, the antibody is pembrolizumab and is contained in a liquid formulation where each 1 mL of solution contains 25 mg of pembrolizumab and is formulated in: L-histidine (1.55 mg), polysorbate 80 (0.2 mg), sucrose (70 mg), and sterile Water for Injection, USP.

In another embodiment, the pharmaceutical carrier for the antibody formulation may include, for example, glacial acetic acid, L-histidine, sucrose, and polysorbate 80. In one particular embodiment, the antibody is formulated in a liquid solution at pH 5.8 where each 1 mL of solution contains glacial acetic acid (16.5 mg), L-histidine (62 mg), sucrose (821.6 mg), polysorbate 20 (8 mg). In a further embodiment, the antibody is atezolizumab and is contained in a liquid formulation where each 1 mL of solution contains glacial acetic acid (16.5 mg), L-histidine (62 mg), sucrose (821.6 mg), polysorbate 20 (8 mg), pH 5.8.

Cancers

Cancers that may be treated according to the methods of the invention and cancers for which a patient's responsiveness to a treatment therapy can be determined according to the methods of the invention include melanoma (including unresectable or metastatic melanoma), prostate cancer, lung cancer (including non-small cell lung cancer and metastatic non-small cell lung cancer) adrenal cancer, anal cancer, bile duct cancer, bladder cancer, bone cancer, cancer of the brain or central nervous system, basal cell skin cancer, breast cancer, cervical cancer, colorectal cancer, endometrial cancer, esophageal cancer, eye cancer, gallbladder cancer, gastrointestinal carcinoid tumors, gastrointestinal stromal tumor (GIST), gastric cancer, glioma, glioblastoma, head and neck cancer (including head and neck squamous cell carcinoma), Hodgkin disease, Classical Hodgkin Lymphoma, diffuse large B cell lymphoma, follicular lymphoma, Kaposi sarcoma, kidney cancer, laryngeal and hypopharyngeal cancer, leukemia (including acute myeloid leukemia), liver cancer (including hepatocellular carcinoma), lymphoma, malignant mesothelioma, merkel cell carcinoma, metastatic urothelial carcinoma, multiple myeloma, myeloma, myelodysplastic syndrome, nasal cavity and paranasal sinus cancer, nasopharyngeal cancer, neuroendocrine cancer, neuroblastoma, non-Hodgkin lymphoma, oral cavity and oropharyngeal cancer, osteosarcoma, ovarian cancer, pancreatic cancer, penile cancer, pituitary tumors, renal cancer (including renal cell carcinoma), retinoblastoma, rhabdomyosarcoma, salivary gland cancer, sarcoma, squamous cell skin cancer, small intestine cancer, stomach cancer, testicular cancer, thymus cancer, thyroid cancer, uterine cancer, or vaginal cancer.

EXAMPLES

Example 1. Patient Response Based on Chi Square Analysis of Biomarkers

Genetic analysis of 85 cancer patients was performed to determine the germ-line variants carried by those patients. Patients were categorized as responders (complete, partial) or non-responders (progressive, stable) to a variety of anti-PD1 and anti-PDL1 antibody therapies including nivolumab, pembrolizumab, durvalumab, and atezolizumab. An extensive panel of biomarkers was tested for each patient, and the biomarkers were analyzed to evaluate the correlation between response to therapy and each of these biomarkers. A chi-square analysis was performed to determine the significance by p values of various biomarkers as correlating with the patient's response, or non-response to treatment. The results of a subset of these tested biomarkers are shown in Table 1 below.

TABLE 1

Response: Independent Chi-Square Tests

| Marker | Chi-Square Value | P Value |
| --- | --- | --- |
| IL18R1/rs11465660 | 4.812 | 0.065 |
| CD44/rs11821102 | 4.949 | 0.068 |
| IL10RB/rs2834167 | 5.100 | 0.088 |
| EXO1/rs4150021 | 3.241 | 0.094 |
| RAD23A/rs8240 | 3.057 | 0.104 |
| IL10/rs4073 | 4.149 | 0.132 |
| STAT3/rs3744483 | 2.957 | 0.236 |
| CD274/rs4742098 | 2.890 | 0.321 |
| miR99a promoter | 1.787 | 0.452 |

P values closer to 0.05, and preferably lower than 0.05, are indicative of greater significance of the correlation between the patient's genotype and their response to the anti-PDL1 or anti-PD1 therapy. As shown in Table 1, IL18R1/rs14465660, CD44/rs11821102, and IL10RB/rs11821102 had the lowest p values, indicating that these biomarkers had the strongest correlation with response, although the other markers were also found to be relevant to determining a patient's likelihood of response to an immune modulating therapy.

Example 2. Biomarker-Driven Identification of Positive Responders

The purpose of this example was to find a prognostic rule that would assign patients a probability of responding to treatment given a panel of genetic signatures. Two classification techniques which are immediately applicable to the case of categorical predictors were used and compared: classification trees and random forests.

Table 2 below is a summary of the comparison of classification strategies showing the accuracy, sensitivity, and specificity for each model based on the number of patients, the number of markers analyzed, and the mutations considered.

TABLE 2

Response: Classification performance estimated via leave-one-out cross-validation

| Method | Accuracy | Sensitivity | Specificity |
| --- | --- | --- | --- |
| 22 Markers-83 Patients-0/1/2* mutations | | | |
| Classification Trees | 0.61 | 0.57 | 0.64 |
| Random Forests | 0.63 | 0.68 | 0.57 |
| 22 Markers-83 Patients-0/1** mutations | | | |
| Classification Trees | 0.69 | 0.66 | 0.7 |
| Random Forests | 0.57 | 0.57 | 0.57 |

*0 = wild type; 1 = heterozygous for mutation; 2 = homozygous for mutation
**0 = wild type; 1 = heterozygous or homozygous for mutation

Example 3. Tree-Based Classification Rule for Predicting Response

Tree-based classification provides an intuitive and easily interpreted prognostic rule. Each leaf of the tree provides a probability of response to treatment and the proportion of the sample falling into each leaf category. FIG. 2 shows a tree-based classification rule for response to anti-PD1 or anti-PDL1 antibody therapy based on the analysis of 22 markers for all 85 patients in the study. The tree provides a method for prognosticating a patient's response to treatment based on 4 genes—CD44, IL18R1, miR99a promoter, and EXO1.

As shown in FIG. 2, CD44 is the first gene of predictive value. If a patient is heterozygous (1) for CD44/rs11821102, the patient is considered a non-responder (by following "yes" and travelling left on the tree). This node of the tree shows a likelihood of response of 0% based on 5 patients (6% of 85). In contrast, if the patient is not heterozygous (0, 2), other markers should be considered before determining whether the patient will be predicted as a responder or non-responder.

If the patient is not heterozygous (0, 2) for CD44/rs11821102, then the presence or absence of IL18R1/rs11465660 should next be determined. If the patient is homozygous wild-type (0) or homozygous for IL18R1/rs11465660 (2), other markers should be considered before determining whether the patient will be predicted as a responder or non-responder. In contrast, if the patient is heterozygous (1) for IL18R1/rs11465660, then the patient is considered a responder. On this node of the tree, the likelihood of response is 75% based on 12 patients (14% of 85 patients).

If the patient is homozygous wild-type (0) or homozygous for IL18R1/rs11465660 (2), then the presence or absence of the miR99a promoter mutation should be determined. If the patient is homozygous (2) for miR99a promoter mutation (or no data is available), then the patient is considered a non-responder as this node of the tree indicates a likelihood of response of 25% (based on 12 of 85 patients). If the patient is heterozygous for miR99a promoter mutation (1) or is homozygous wild-type (0), then other markers should be considered before determining whether the patient will be predicted as a responder or non-responder.

If the patient is heterozygous for miR99a promoter mutation (1) or is homozygous wild-type (0), then the presence or absence of the EXO1 mutation should be determined. If the patient is heterozygous (1) for the EXO1 mutation (or no data is available), then the patient is considered a medium responder, as this node of the tree indicates a likelihood of response of 43% (based on 19 of 85 patients). If the patient is homozygous (2) for the EXO1 mutation or homozygous wild-type (0), then the patient is considered a responder as this node of the tree indicates a likelihood of response of 55% (based on 37 of 85 patients). Accordingly, patients who are homozygous wild-type or homozygous for the EXO1 mutation are considered to have better response rates than patients heterozygous for the EXO1 mutation provided the upstream parameters are met.

Example 4. Variable Importance of Response Biomarkers

The variable importance of each biomarker was assessed. Variable importance is measured as the normalized reduction in cross validated entropy as each marker is added to a classification tree. The results are shown in Table 3. The higher the value, the more important the mutation is as a relevant indicator predictive of response to an immune modulating agent. Thus, some biomarkers that are not predicted by the tree method of Example 3, may still be important in predicting a patient's response to an immune modulating therapy.

Based on the overall values generated, the mutations in Table 3 may be considered significant with respect to predicting the response of a cancer patient to an immune modulating agent including, but not limited to, an anti-PDL1 or anti-PD1 antibody therapy.

TABLE 3

| Variable Importance | |
| --- | --- |
| Mutation | Overall |
| IL8/rs4073 | 9.303750 |
| RAD23A/rs8240 | 6.311548 |
| CD274/rs4742098 | 4.892502 |
| STAT3/rs3744483 | 5.980581 |

Based on these values, the IL8, RAD23A, CD274, and STAT3 biomarkers disclosed may be considered significant with respect to predicting response of a patient to an immune modulating agent such as, but not limited to, an anti-PDL1 or anti-PD1 antibody therapy.

Example 5. Confirmation of Significance of Response Biomarkers

In a separate study, genetic analysis was performed to determine the germ-line variants carried by 55 cancer patients using anti-PD1 and anti-PDL1 antibody therapies including nivolumab, pembrolizumab, durvalumab, and atezolizumab. A panel of 29 biomarkers was tested for each patient, and marginal chi-square analysis was used to evaluate the correlation between response to therapy and each of these biomarkers.

As in the prior examples, CD274/rs4742098, IL18R1/rs11465660, EXO1/rs4150021, STAT3/rs3744483, miR99a promoter, and IL10RB/rs2834167 were relevant to determining a patient's likelihood of response to an immune modulating therapy. CD274/rs4742098, IL18R1/rs11465660, and EXO1/rs4150021 had the lowest p values, indicating that these biomarkers had the strongest correlation with response.

TABLE 4

| Response: Marginal Chi-Square Tests Comparing No Response (NR) and Response (R) Groups | | | | | | | |
| --- | --- | --- | --- | --- | --- | --- | --- |
| Marker | NR: 0 | NR: 1 | NR: 2 | R: 0 | R: 1 | R: 2 | P Value |
| CD274/rs4742098 | 15 | 18 | 0 | 18 | 4 | 0 | 0.014 |
| IL18R1/rs11465660 | 30 | 3 | 0 | 14 | 8 | 0 | 0.022 |
| EXO1/rs4150021 | 21 | 12 | 0 | 20 | 2 | 0 | 0.035 |
| STAT3/rs3744483 | 24 | 5 | 4 | 13 | 9 | 0 | 0.043 |
| miR99a promoter | 6 | 18 | 9 | 10 | 9 | 3 | 0.082 |
| IL10RB/rs2834167 | 10 | 18 | 5 | 12 | 8 | 2 | 0.226 |

Of the 55 cancer patients analyzed, several statistical classifiers were trained on 36 cancer patients who were progression-free following six months of treatment. Biomarkers were treated either as categorical variables (i.e., wild type, heterozygous mutant, or homozygous mutant) or continuous variables by assigning a value of 0 to wild type, 1 to heterozygous mutants, and 2 to homozygous mutants. Predictive models were fit for each type of biomarker data. Two sets of classification trees were tuned separately on minimum split and minimum node size across a discrete grid ranging from 1 to 30 and 1 to 20, respectively. Logistic regression models with LASSO (least absolute shrinkage and selection operator) penalty were tuned on the regularization parameter lambda. During training, tuning parameters were selected to maximize predictive accuracy using leave-one-out cross validation. Classification trees and LASSO models were fit in R (version 3.3.2) calling rpart (version 4.1-11) and glmnet (version 2.0-10), respectively. The accuracy, sensitivity, and specificity for each is shown in Table 5 below.

TABLE 5

| Response: Classification performance estimated via leave-one-out cross-validation | | | |
| --- | --- | --- | --- |
| Method | Accuracy | Sensitivity | Specificity |
| 29 Markers-36 Patients-0/1/2* mutations | | | |
| Classification Trees | 0.757 | 0.700 | 0.804 |
| LASSO Models | 0.730 | 0.633 | 0.804 |
| 29 Markers-36 Patients-0/1** mutations | | | |
| Classification Trees | 0.757 | 0.700 | 0.804 |
| LASSO Models | 0.730 | 0.633 | 0.804 |

*0 = wild type; 1 = heterozygous for mutation; 2 = homozygous for mutation
**0 = wild type; 1 = heterozygous or homozygous for mutation These results indicate that the biomarkers listed above, and in particular CD274/rs4742098, are particularly useful in predicting patients who would have a lasting response to immunotherapy versus those who would not.

Example 6: Toxicity Prediction Based on Chi Square Analysis of Biomarkers

Genetic analysis of 90 cancer patients was performed to determine the SNP biomarkers carried by those patients. Patients were categorized as having a toxic response (Grade of 2 or higher) or having a non-toxic response (Grade 0 or 1) to a variety of anti-PD1 and anti-PDL1 antibody therapies including nivolumab, pembrolizumab, durvalumab, and atezolizumab. An extensive panel of biomarkers was tested for each patient, and the biomarkers were analyzed to evaluate the correlation between a patient's toxicity score and each of these biomarkers. A chi-square analysis was performed to determine the significance by p values of various biomarkers as correlating with the patient's level of toxic response on the scale of Grades 0-5. The results of a subset of these tested biomarkers are shown in Table 6 below.

TABLE 6

| Toxicity: Independent Chi-Square Tests | | |
| --- | --- | --- |
| Marker | Chi-Square Value | P Value |
| KRAS/rs61764370 | 6.423 | 0.020 |
| FCGR2A/rs10919033 | 6.022 | 0.024 |
| CD274/rs4742098 | 4.757 | 0.029179 |

TABLE 6-continued

Toxicity: Independent Chi-Square Tests

| Marker | Chi-Square Value | P Value |
|---|---|---|
| TRL4/rs4986790 | 4.867 | 0.056 |
| EREG/rs1460008 | 5.933 | 0.066 |
| RAC1/rs9374 | 5.008 | 0.071 |
| miR99a/promoter | 4.330 | 0.121 |
| IL10RB/rs2834167 | 3.375 | 0.196 |
| MSH2/rs2303428 | 2.728 | 0.339 |

P values closer to 0.05, and preferably lower than 0.05, are indicative of greater significance of the correlation between the patient's genotype and their toxic response to the anti-PDL1 or anti-PD1 therapy. As shown in Table 4, KRAS/rs61764370, FCGR2A/rs10919033, CD274/rs4742098, and TLR4/rs4986790 had the lowest p values, indicating that these biomarkers had the strongest correlation with toxicity, although the other markers were also found to be relevant to determining a patient's likelihood of having a toxic response to an immune modulating therapy.

With respect to CD274/rs4742098, being homozygous for the marker correlates with an increased likelihood of toxicity.

Example 7. Biomarker-Driven Identification of Toxic Response

The purpose of this example was to find a prognostic rule that would assign patients a probability of having a toxic response (Grade 2 or higher) to an immune modulating agent given a panel of genetic signatures. Two classification techniques which are immediately applicable to the case of categorical predictors were used and compared: classification trees and random forests.

Table 5 below is a summary of the comparison of classification strategies showing the accuracy, sensitivity, and specificity for each model based on the number of patients, the number of markers analyzed, and the mutations considered.

TABLE 7

Toxicity: Classification performance estimated via leave-one-out cross-validation

| Method | Accuracy | Sensitivity | Specificity |
|---|---|---|---|
| 50 Markers-87 Patients-0/1 mutations | | | |
| Classification Trees | 0.67 | 0.72 | 0.56 |
| Random Forests | 0.68 | 0.93 | 0.21 |
| 46 Markers-90 Patients-0/1 mutations | | | |
| Classification Trees | 0.73 | 0.83 | 0.53 |
| Random Forests | 0.65 | 0.89 | 0.18 |

0 = wild type; 1 = heterozygous or homozygous for mutation

Example 8. Tree-Based Classification Rule for Predicting Toxicity

Figure 3:
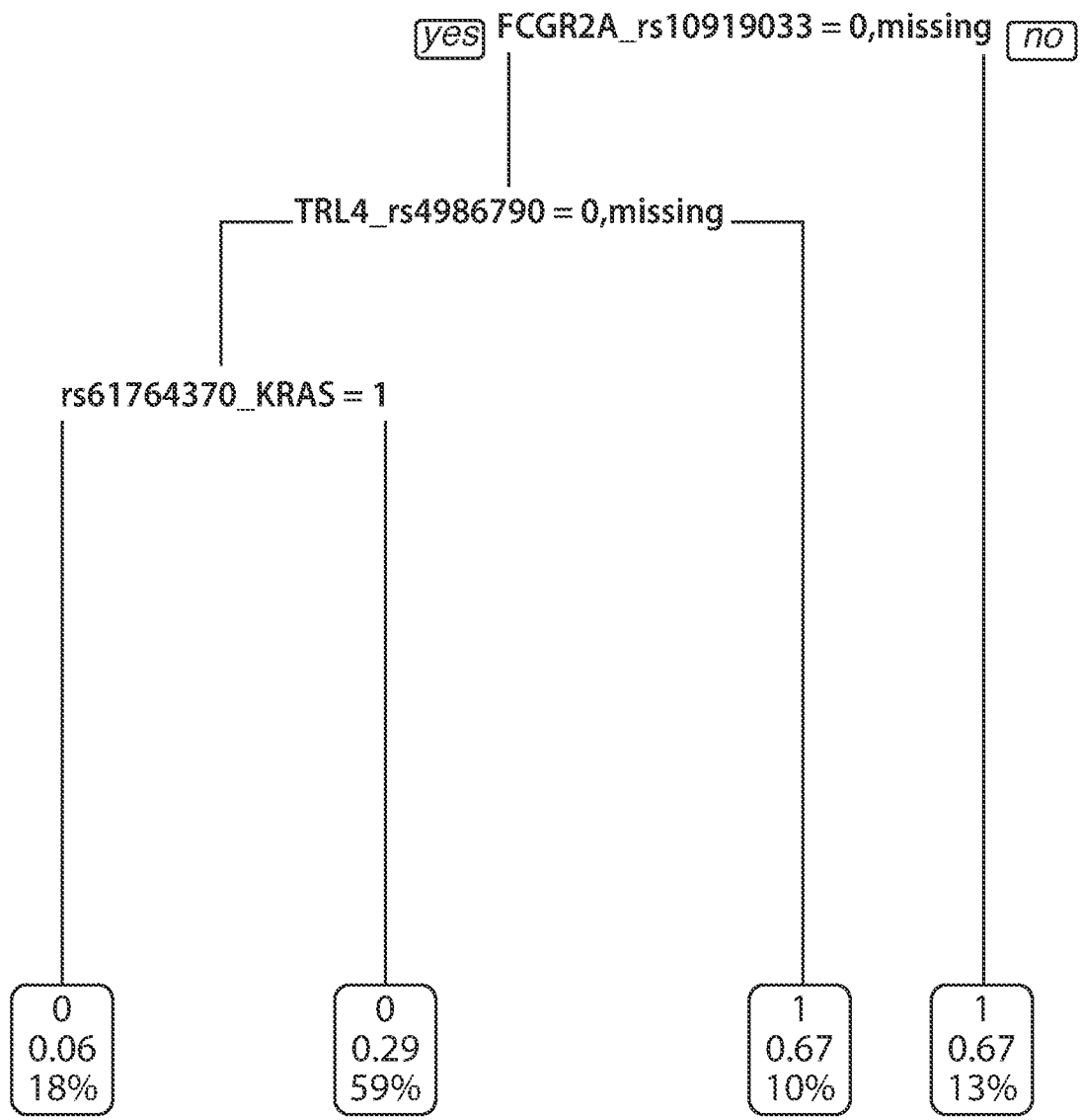
FIG. 3 is a tree-based classification rule providing a prognostic indication of whether or not a patient will have a toxic response to treatment with an immune modulating agent. Each leaf of the tree provides a probability of a toxic response based on the presence of absence of the particular biomarker as indicated therein, i.e., FCGR2A/rs10919033, TLR4/rs4986790, and KRAS/rs61764370. "0" means the patient is homozygous wild-type. "1" means the patient carries one or two copies of the mutation, i.e., the patient is homozygous or heterozygous for the mutation. "Missing" means no data is available for the patient.

Tree-based classification provides an intuitive and easily interpreted prognostic rule. Each leaf of the tree provides a probability of response to treatment and the proportion of the sample falling into each leaf category. FIG. 3 shows a tree-based classification rule for response to anti-PD1 or anti-PDL1 antibody therapy based on the analysis of 50 markers for all 90 patients in the study. The tree provides a method for prognosticating a patient's likelihood of a toxic response to treatment based on 3 genes—KRAS, TLR4, and FCGR2A.

As shown in FIG. 2, FCGR2A is the first gene of predictive value. If a patient is heterozygous or homozygous (1) for FCGR2A/rs10919033, the patient is considered to have a strong likelihood of a toxic response (by following "no" and travelling right on the tree). This node of the tree shows a likelihood of toxic response of 67% based on 12 patients (13% of 90). In contrast, if the patient is homozygous wild-type (0), e.g., the patient does not carry the mutation (or no data is available) other markers should be considered before determining the patient's likelihood of having a toxic response.

If the patient is homozygous wild-type (0), e.g., the patient does not carry the mutation, for FCGR2A/rs10919033 (or no data is available) then the presence or absence of TLR4/rs4986790 should be determined. If the patient is homozygous wild-type (0) (or no data is available) for FCGR2A/rs10919033, other markers should be considered before determining whether the patient will be predicted as having a toxic versus non-toxic response. In contrast, if the patient is heterozygous or homozygous (1) for TLR4/rs4986790, then the patient is considered to be a toxic responder. On this node of the tree, the likelihood of a toxic response is 67% based on 9 patients (10% of 90 patients).

If the patient is homozygous wild-type (0) (or no data is available) for TLR4/rs4986790, then the presence or absence of KRAS/rs61764370 should be determined. If the patient is homozygous for wild-type (0), then the patient is not considered to have a low likelihood of a toxic response as this node of the tree indicates a likelihood of toxic response of 29% (based on 53 of 90 patients). If the patient is homozygous or heterozygous (1) for KRAS/rs61764370, then the patient is considered to have a low likelihood of toxic response as this node of the tree indicates a likelihood of toxic response of 6% (based on 16 of 90 patients). Such patients may be predicted to have a non-toxic response.

Example 9. Variable Importance of Toxicity Biomarkers

The variable importance of each biomarker was assessed. Variable importance is measured as the normalized reduction in cross validated entropy as each marker is added to a classification tree. The results are shown in Table 6. The higher the value, the more important the mutation as an indicator of toxic response to an immune modulating agent. Thus, some biomarkers that are not predicted by the tree method of Example 7, may still be important in predicting whether or not a patient will have a toxic response to an immune modulating therapy.

Based on the overall values generated, the mutations in Table 8 may be considered significant with respect to predicting the toxic response of a cancer patient to an immune modulating agent, for example, an anti-PDL1 or anti-PD1 antibody therapy.

TABLE 8

| Variable Importance | |
| --- | --- |
| Mutation | Overall |
| FCGR2A/rs1801274 | 9.378820 |
| MSH2/rs2303428 | 9.395148 |
| IL10RB/rs2834167 | 4.736778 |

Based on these values, the FCGR2A, IL10RB, and MSH2 mutations disclosed may be considered significant with respect to predicting the toxic response of a patient to an immune modulating agent such as, but not limited to, an anti-PDL1 or anti-PD1 antibody therapy.

Example 10. Predicting Toxicity to Radiation Therapy

Genetic analysis of 90 cancer patients was performed to determine the biomarkers carried by those patients. Patients receiving radiation therapy as a treatment for cancer were categorized as having a toxic response (Grade of 2 or higher) or having a non-toxic response (Grade 0 or 1). An extensive panel of biomarkers was tested for each patient, and the biomarkers were analyzed to evaluate the correlation between a patient's radiation toxicity score and each of these biomarkers. A chi-square analysis was performed to determine the significance by p values of various biomarkers as correlating with the patient's level of toxic response to radiation. The results of a subset of these tested biomarkers are shown in Table 9 below.

TABLE 9

| Markers Correlating with Radiation Toxicity | |
| --- | --- |
| Marker | P Value |
| CD274/rs4742098 | <0.0005 |
| IL10RB/rs2834167 | 0.065357 |
| TRL4/rs4986790 | 0.101359 |

P values closer to 0.05, and preferably lower than 0.05, are indicative of greater significance of the correlation between the patient's genotype and whether or not they had a toxic response to radiation therapy. As shown in Table 7, the p values for CD274/rs4742098, IL10RB/rs2834167, and TLR4/rs4986790 demonstrate that these markers have a strong correlation with a patient's toxicity score with respect to radiation, and are therefore relevant in assessing a patient's likelihood of a toxic response to radiation therapy.

The analysis of these markers also showed that for TLR4/rs4986790, a patient experiences a protective effect against radiation toxicity if the patient is heterozygous or homozygous for the marker, as the marker acts in a dominant fashion.

The analysis of these markers also showed that for CD274/rs4742098, the patient is at risk for a toxic response to radiation if the patient is homozygous for the marker, as the marker acts in a recessive fashion.

The analysis of these markers also showed that for IL10RB/rs2834167, the patient is at risk for a toxic response to radiation if the patient is homozygous for the marker, as the marker acts in a recessive fashion.

Example 11. Biomarker-Driven Identification of Toxic Response is not Specific to Cancer Type An analysis of biomarkers associated with toxic response to anti-PD1 and anti-PDL1 antibody therapies (including nivolumab, pembrolizumab, durvalumab, and atezolizumab) was performed across a variety of cancers, including melanoma and prostate. As in the prior example, RAC1/rs9374, KRAS/rs61764370, and FCGR2A/rs10919033 were relevant to determining a patient's likelihood of a toxic response to an immune modulating therapy across a variety of cancers.

Of the biomarkers tested, RAC1-rs9374 was most strongly associated with toxicity response across all cancer types. P values for RAC1-rs9374 were calculated using marginal chi-square tests comparing not toxic and toxic groups and found to be 0.001 for the melanoma dataset (54 patients), 0.046 for the prostate cancer dataset (30 patients), and 0.001 for the dataset for all other cancers (49 patients), for an overall p value of 0.000 across cancer types.

Several statistical classifiers were trained on the total set of cancer patients evaluated for toxicity. Subjects were classified as experiencing high toxicity (highest grade of 2 or more) versus low toxicity (highest grade less than 2). Predictive models of high-grade toxicity were based on common markers between training and test samples. Biomarkers were treated either as categorical variables (i.e., wild type, heterozygous mutant, or homozygous mutant) or continuous variables by assigning a value of 0 to wild type, 1 to heterozygous mutants, and 2 to homozygous mutants. Predictive models were fit for each type of biomarker data. Two sets of classification trees were tuned separately on minimum split and minimum node size across a discrete grid ranging from 1 to 30 and 1 to 20, respectively. Logistic regression models with LASSO penalty were tuned on the regularization parameter lambda. During training, tuning parameters were selected to maximize predictive accuracy using leave-one-out cross validation. CT and LASSO models were fit in R (version 3.3.2) calling rpart (version 4.1-11) and glmnet (version 2.0-10), respectively. A total of six missing SNP values were imputed via chained equations with SNPs treated as categorical variables. Imputation was performed in R calling mi (version 1.0) with a maximum of 20 iterations. The final misclassification error rates were estimated on validation data not used in training. The accuracy, sensitivity, and specificity for each is shown in Table 12 below.

TABLE 10

| Toxicity Across Cancer Types: Classification performance estimated via leave-one-out cross-validation | | | |
| --- | --- | --- | --- |
| Method | Accuracy | Sensitivity | Specificity |
| Classification Trees (Training) | 0.723 | 0.736 | 0.700 |
| Classification Trees (Validation) | 0.805 | 0.776 | 0.885 |
| LASSO (Training) | 0.723 | 0.736 | 0.700 |
| LASSO (Validation) | 0.805 | 0.776 | 0.885 |

These results provide further evidence of the significance of the above-identified biomarkers in predicting whether a patient has a decreased likelihood of a toxic response to cancer treatment with an immune modulating agent, and show that this prediction holds regardless of the type of cancer being treated.

In a specific embodiment, these results indicate that a patient who does not carry an A nucleotide at a position corresponding to position 101 of SEQ ID NO:15 (RAC1/rs9374), has a decreased likelihood of a toxic response to cancer treatment with an immune modulating agent, regardless of the type of cancer being treated

What is claimed is:

1. A method of treating cancer comprising administering an anti-PD1 or anti-PDL1 antibody to a patient identified as carrying or not carrying one or more mutations selected from:
   a. not carrying the EXO1 gene SNP rs4150021, wherein rs4150021 comprises SEQ ID NO: 19 with a deletion of a T nucleotide at a position 101 of SEQ ID NO:19;
   b. not carrying the IL10RB gene SNP rs2834167, wherein rs2834167 comprises SEQ ID NO: 6 with a G nucleotide at a position 101 of SEQ ID NO:6; or
   c. carrying the STAT3 gene SNP rs3744483, wherein rs3744483 comprises SEQ ID NO: 10 with a C nucleotide at position 101 of SEQ ID NO:10.

2. The method of claim 1, wherein the patient is identified as heterozygous for a deletion of a T nucleotide at position 101 of SEQ ID NO:19 or is identified as not heterozygous for a deletion of a T nucleotide at position 101 of SEQ ID NO: 19.

3. The method of claim 1, wherein the cancer is melanoma.

4. The method of claim 1, wherein the cancer is prostate cancer.

5. The method of claim 1, wherein the cancer is lung cancer.

6. The method of claim 1, wherein the cancer is selected from melanoma, prostate cancer, lung cancer, adrenal cancer, anal cancer, bile duct cancer, bladder cancer, bone cancer, cancer of the brain/CNS, basal cell skin cancer, breast cancer, cervical cancer, colorectal cancer, endometrial cancer, esophageal cancer, eye cancer, gallbladder cancer, gastrointestinal carcinoid tumors, gastrointestinal stromal tumor (GIST), gastric cancer, glioma, glioblastoma, head and neck cancer, Hodgkin disease, Kaposi sarcoma, kidney cancer, laryngeal and hypopharyngeal cancer, leukemia, liver cancer, lymphoma, malignant mesothelioma, merkel cell carcinoma, metastatic urothelial carcinoma, multiple myeloma, myeloma, myelodysplastic syndrome, nasal cavity and paranasal sinus cancer, nasopharyngeal cancer, neuroendocrine cancer, neuroblastoma, non-Hodgkin lymphoma, oral cavity and oropharyngeal cancer, osteosarcoma, ovarian cancer, pancreatic cancer, penile cancer, pituitary tumors, renal cancer, retinoblastoma, rhabdomyosarcoma, salivary gland cancer, sarcoma, squamous cell skin cancer, small intestine cancer, stomach cancer, testicular cancer, thymus cancer, thyroid cancer, uterine cancer, or vaginal cancer.

7. The method of claim 1, wherein the patient is a human.

8. A reduced-toxicity method of cancer treatment comprising administering an anti-PD1 or anti-PDL1 antibody to a patient suffering from cancer, wherein the patient is identified as carrying or not carrying one or more mutations selected from the group consisting of:
   a. not carrying the IL10RB gene SNP rs2834167, wherein rs2834167 comprises SEQ ID NO: 6 with a G nucleotide at a position 101 of SEQ ID NO:6;
   b. not carrying the FCGR2A gene SNP rs10919033, wherein rs10919033 comprises SEQ ID NO: 12 with a C nucleotide at position 101 of SEQ ID NO: 12;
   c. not carrying the TLR4 gene SNP rs4986790, wherein rs4986790 comprises SEQ ID NO: 16 with a G nucleotide at position 101 of SEQ ID NO: 16; or
   d. not carrying the EREG gene SNP rs1460008, wherein rs1460008 comprises SEQ ID NO: 11 with a G nucleotide at position 101 of SEQ ID NO: 11.

9. The method of claim 8, wherein the patient is identified as neither heterozygous nor homozygous for a C nucleotide at position 101 of SEQ ID NO: 12.

10. The method of claim 8, wherein the patient is identified as neither heterozygous nor homozygous for a G nucleotide at position 101 of SEQ ID NO: 16.

11. The method of claim 8, wherein the cancer is melanoma.

12. The method of claim 8, wherein the cancer is prostate cancer.

13. The method of claim 8, wherein the cancer is lung cancer.

14. The method of claim 8, wherein the cancer is selected from melanoma, prostate cancer, lung cancer, adrenal cancer, anal cancer, bile duct cancer, bladder cancer, bone cancer, cancer of the brain/CNS, basal cell skin cancer, breast cancer, cervical cancer, colorectal cancer, endometrial cancer, esophageal cancer, eye cancer, gallbladder cancer, gastrointestinal carcinoid tumors, gastrointestinal stromal tumor (GIST), gastric cancer, glioma, glioblastoma, head and neck cancer, Hodgkin disease, Kaposi sarcoma, kidney cancer, laryngeal and hypopharyngeal cancer, leukemia, liver cancer, lymphoma, malignant mesothelioma, merkel cell carcinoma, metastatic urothelial carcinoma, multiple myeloma, myeloma, myelodysplastic syndrome, nasal cavity and paranasal sinus cancer, nasopharyngeal cancer, neuroendocrine cancer, neuroblastoma, non-Hodgkin lymphoma, oral cavity and oropharyngeal cancer, osteosarcoma, ovarian cancer, pancreatic cancer, penile cancer, pituitary tumors, renal cancer, retinoblastoma, rhabdomyosarcoma, salivary gland cancer, sarcoma, squamous cell skin cancer, small intestine cancer, stomach cancer, testicular cancer, thymus cancer, thyroid cancer, uterine cancer, or vaginal cancer.

15. The method of claim 8, wherein the patient is a human.

* * * * *

SEQUENCE LISTING

```
Sequence total quantity: 34
SEQ ID NO: 1                  moltype = DNA   length = 201
FEATURE                       Location/Qualifiers
source                        1..201
                              mol_type = genomic DNA
                              organism = Homo sapiens
SEQUENCE: 1
aacttatgtg cttaacaggc aatgcttctc agaccacaaa gcagaaagaa gaagaaaagc    60
tcctgactaa atcagggctg ggcttagaca gagttgatct atagaatatc tttaaaggag   120
agatgtcaac tttctgcact attcccagcc tctgctcctc cctgtctacc ctctcccctc   180
cctctctccc tccacttcac c                                             201

SEQ ID NO: 2                  moltype = DNA   length = 201
FEATURE                       Location/Qualifiers
source                        1..201
                              mol_type = genomic DNA
                              organism = Homo sapiens
SEQUENCE: 2
cataggcaga gatgataccT aattctgcat ttgattgtca ctttttgtac ctgcattaat    60
ttaataaaat attcttattt attttgttac ttggtacacc ggcatgtcca ttttcttgtt   120
tattttgtgt ttaataaaat gttcagttta acatcccagt ggagaaagtt acttggaata   180
tttgcagcct tgttcctagt t                                             201

SEQ ID NO: 3                  moltype = DNA   length = 200
FEATURE                       Location/Qualifiers
source                        1..200
                              mol_type = genomic DNA
                              organism = Homo sapiens
SEQUENCE: 3
caagagaatc tgatcaattt gaagtccctg tttgggaatg aggcacttat cagcatgaag    60
aattttttct cattctgtgc catttttaaaa atagaatacA tttgtatatt aactttaaa   120
ttgggttgtg gttttttgc tcagcttttt atattttat aagaagctaa atagaagaat    180
aattgtatct ctgacaggtt                                               200

SEQ ID NO: 4                  moltype = DNA   length = 201
FEATURE                       Location/Qualifiers
source                        1..201
                              mol_type = genomic DNA
                              organism = Homo sapiens
SEQUENCE: 4
aagaaaatca tccatgatct tgttctaaca cctgccactc tagtactata tctgtcacat    60
ggtactatga taaagttatc tagaaataaa aaagcataca attgataatt caccaaattg   120
tggagcttca gtatttttaaa tgtatattaa aattaaatta ttttaaagat caagaaaaac   180
tttcgtcata ctccgtatttt g                                            201

SEQ ID NO: 5                  moltype = DNA   length = 201
FEATURE                       Location/Qualifiers
source                        1..201
                              mol_type = genomic DNA
                              organism = Homo sapiens
SEQUENCE: 5
aaaaattata atattgggct tctttctaaa tcgttcacag agaagctcag taaataaata    60
gaaatggggg ttgaggtatc agaggtaata aatattctat gagagaggta caataaggtt   120
tctcaagggg ctgggtcagc tatcccagag ccccagatcc gattttggag acctctaatt   180
tatgtcctag agtctataga g                                             201

SEQ ID NO: 6                  moltype = DNA   length = 201
FEATURE                       Location/Qualifiers
source                        1..201
                              mol_type = genomic DNA
                              organism = Homo sapiens
SEQUENCE: 6
tattttcata gcattgggaa tggtaccacc tcccgaaaat gtcagaatga attctgttaa    60
tttcaagaac attctacagt gggagtcacc tgcttttgcc gaagggaacc tgactttcac   120
agctcagtac ctaaggtggg tctggcctca ctattggcag gaacgcaccg gaggagccag   180
ccctgggctg gtcactgggt t                                             201

SEQ ID NO: 7                  moltype = DNA   length = 201
FEATURE                       Location/Qualifiers
source                        1..201
                              mol_type = genomic DNA
                              organism = Homo sapiens
SEQUENCE: 7
ttggcataag gcagcatggt gtggcagtta agagatgggc tgtgcagccc atcctgagct    60
ccagtcctga gtttgctact tacttctgtg gcctctggaa acttatccaa cctcttggtg   120
cttcagtttc ctcatctgtg aaattagaat ttataatat tgcacctacc tcccaggggt   180
aactaaatga ataaatataa t                                             201
```

| SEQ ID NO: 8 | moltype = DNA length = 201 |
| --- | --- |
| FEATURE | Location/Qualifiers |
| source | 1..201 |
| | mol_type = genomic DNA |
| | organism = Homo sapiens |

SEQUENCE: 8

```
caagggggt ggagggagag cggggaagga gggggtgtca gctcaactgt aaaagctgca    60
cagatttttt ttctttctct ctctctgcct ctccatagat cgtttctgtt tcatgccctg   120
tctcatttcg catagctaaa aaagaatgct aattaagatc ccttgtctta acctgaaaaa   180
taatgactcg gctgtaatta g                                             201
```

| SEQ ID NO: 9 | moltype = DNA length = 201 |
| --- | --- |
| FEATURE | Location/Qualifiers |
| source | 1..201 |
| | mol_type = genomic DNA |
| | organism = Homo sapiens |

SEQUENCE: 9

```
gagggaagc tggagcccca actttgatcc tccattggag tggcccaaat ctttccatct    60
agggcaagtc ctgaaaggcc caaggccccc tccccagtct agccttggcc tccagcctgg   120
agaagggcta acatcagctc attgtcaagg ccaccccccac cccagaacag aaccgtgtct   180
ctgataaagg ttttgaagtg a                                             201
```

| SEQ ID NO: 10 | moltype = DNA length = 201 |
| --- | --- |
| FEATURE | Location/Qualifiers |
| source | 1..201 |
| | mol_type = genomic DNA |
| | organism = Homo sapiens |

SEQUENCE: 10

```
cgtcgctggg gccccatagt gtgcatcatg tccaacctgt aactctctcc ccctcttctt    60
ccatgaggtc ctgagaccag gattcctaaa acaaacagga cgaggaccct ttagacacgc   120
aaggagacat gcctctagca ggatcagggg gactggggtc gggagggtgg ggcaggaagg   180
aagccagaat cagaagtatc c                                             201
```

| SEQ ID NO: 11 | moltype = DNA length = 201 |
| --- | --- |
| FEATURE | Location/Qualifiers |
| source | 1..201 |
| | mol_type = genomic DNA |
| | organism = Homo sapiens |

SEQUENCE: 11

```
aagtttgaag agccattttg gtaaacggtt tttattaaag atgctatgga acataaagtt    60
gtattgcatg caatttgaag taacttattt gactatgaat gttatcggat tactgaattg   120
tatcaatttg tttgtgttca atatcagctt tgataattgt gtaccttaag atattgaagg   180
agaaaataga taatttacaa g                                             201
```

| SEQ ID NO: 12 | moltype = DNA length = 201 |
| --- | --- |
| FEATURE | Location/Qualifiers |
| source | 1..201 |
| | mol_type = genomic DNA |
| | organism = Homo sapiens |

SEQUENCE: 12

```
ccatgtcaac agtaataact aaagagtaac gttatgccat gtggtcatac tctcagcttg    60
ctgagtggat gacaaaaaga ggggaattgt taaaggaaaa cttaaatgga gactggaaaa   120
atcctgagca aacaaaacca cctggcccctt agaaatagct ttaactttgc ttaaactaca   180
aacacaagca aaacttcacg g                                             201
```

| SEQ ID NO: 13 | moltype = DNA length = 201 |
| --- | --- |
| FEATURE | Location/Qualifiers |
| source | 1..201 |
| | mol_type = genomic DNA |
| | organism = Homo sapiens |

SEQUENCE: 13

```
aggcttggat gagaacagcg tgtagcctat gtttcctgtg cagtggtaat caccactgtg    60
actgtggttt gcttgtggga tggagaaggt gggatccaaa cggagaatt tctgggattt   120
tccattctgg aagaatgtga ccttgaccag aggcttgtcc ttccagctgt ggcacctcag   180
catgatggtt tctccctcct g                                             201
```

| SEQ ID NO: 14 | moltype = DNA length = 201 |
| --- | --- |
| FEATURE | Location/Qualifiers |
| source | 1..201 |
| | mol_type = genomic DNA |
| | organism = Homo sapiens |

SEQUENCE: 14

```
aggcgtgtgc cactacactc aactaatttt tgtattttta ggagagacgg ggtttcaccc    60
tgttggccag gctggtctcg aactcctgac ctcaagtgat gcaccacct tggcctcata   120
aacctgtttt gcagaactca tttattcagc aaatatttat tgagtgccta ccagatgcca   180
gtcaccacac aaggcactgg g                                             201
```

| SEQ ID NO: 15 | moltype = DNA length = 201 |
| --- | --- |
| FEATURE | Location/Qualifiers |

```
source                  1..201
                        mol_type = genomic DNA
                        organism = Homo sapiens
SEQUENCE: 15
tctaaatgta agagttcaga ctcacattct attaaaattt agccctaaaa tgacaagcct    60
tcttaaagcc ttattttca aaagcgcccc cccattctt attcagatta agagttgcca    120
aaataccttc tgaactacac tgcattgttg tgccgagaac accgagcact gaactttgca   180
aagaccttcg tctttgagaa g                                             201

SEQ ID NO: 16           moltype = DNA   length = 201
FEATURE                 Location/Qualifiers
source                  1..201
                        mol_type = genomic DNA
                        organism = Homo sapiens
SEQUENCE: 16
gaaggaaact tggaaaagtt tgacaaatct gctctagagg gcctgtgcaa tttgaccatt    60
gaagaattcc gattagcata cttagactac tacctcgatg gtattattga cttatttaat   120
tgtttgacaa atgtttcttc atttccctg gtgagtgtga ctattgaaag ggtaaaagac    180
ttttcttata atttcggatg g                                             201

SEQ ID NO: 17           moltype = DNA   length = 201
FEATURE                 Location/Qualifiers
source                  1..201
                        mol_type = genomic DNA
                        organism = Homo sapiens
SEQUENCE: 17
aacttatgtg cttaacaggc aatgcttctc agaccacaaa gcagaaagaa gaagaaaagc    60
tcctgactaa atcagggctg ggcttagaca gagttgatct gtagaatatc tttaaaggag   120
agatgtcaac tttctgcact attcccagcc tctgctcctc cctgtctacc ctctcccctc   180
cctctctccc tccacttcac c                                             201

SEQ ID NO: 18           moltype = DNA   length = 201
FEATURE                 Location/Qualifiers
source                  1..201
                        mol_type = genomic DNA
                        organism = Homo sapiens
SEQUENCE: 18
cataggcaga gatgatacct aattctgcat ttgattgtca cttttttgtac ctgcattaat    60
ttaataaaat attcttattt attttgttac ttggtacacc agcatgtcca ttttcttgtt   120
tattttgtgt ttaataaaat gttcagttta acatcccagt ggagaaagtt acttggaata   180
tttgcagcct tgttcctagt t                                             201

SEQ ID NO: 19           moltype = DNA   length = 201
FEATURE                 Location/Qualifiers
source                  1..201
                        mol_type = genomic DNA
                        organism = Homo sapiens
SEQUENCE: 19
caagagaatc tgatcaattt gaagtccctg tttgggaatg aggcacttat cagcatgaag    60
aatttttct cattctgtgc catttaaaa atagaataca ttttgtatat taactttata   120
attgggttgt ggtttttttg ctcagctttt tatattttta taagaagcta aatagaagaa   180
taattgtatc tctgacaggt t                                             201

SEQ ID NO: 20           moltype = DNA   length = 201
FEATURE                 Location/Qualifiers
source                  1..201
                        mol_type = genomic DNA
                        organism = Homo sapiens
SEQUENCE: 20
aagaaaatca tccatgatct tgttctaaca cctgccactc tagtactata tctgtcacat    60
ggtactatga taaagttatc tagaaataaa aaagcataca tttgataatt caccaaattg   120
tggagcttca gtatttttaaa tgtatattaa aattaaatta ttttaaagat caaagaaaac   180
tttcgtcata ctccgtattt g                                             201

SEQ ID NO: 21           moltype = DNA   length = 201
FEATURE                 Location/Qualifiers
source                  1..201
                        mol_type = genomic DNA
                        organism = Homo sapiens
SEQUENCE: 21
aaaaattata atattgggct tctttctaaa tcgttcacag agaagctcag taaataaata    60
gaaatggggg ttgaggtatc agaggtaata aatattctat aagagaggta caataaggtt   120
tctcaagggg ctgggtcagc tatcccagag ccccagatcc gattttggag acctctaatt   180
tatgtcctag agtctataga g                                             201

SEQ ID NO: 22           moltype = DNA   length = 201
FEATURE                 Location/Qualifiers
source                  1..201
                        mol_type = genomic DNA
```

```
                         organism = Homo sapiens
SEQUENCE: 22
tattttcata gcattgggaa tggtaccacc tcccgaaaat gtcagaatga attctgttaa    60
tttcaagaac attctacagt gggagtcacc tgcttttgcc aaagggaacc tgactttcac   120
agctcagtac ctaaggtggg tctggcctca ctattggcag gaacgcaccg gaggagccag   180
ccctgggctg gtcactgggt t                                             201

SEQ ID NO: 23              moltype = DNA   length = 201
FEATURE                    Location/Qualifiers
source                     1..201
                           mol_type = genomic DNA
                           organism = Homo sapiens
SEQUENCE: 23
ttggcataag gcagcatggt gtggcagtta agagatgggc tgtgcagccc atcctgagct    60
ccagtcctga gtttgctact tacttctgtg gcctctggaa ccttatccaa cctcttggtg   120
cttcagtttc ctcatctgtg aaattagaat ttataataat tgcacctacc tcccaggggt   180
aactaaatga ataaatataa t                                             201

SEQ ID NO: 24              moltype = DNA   length = 201
FEATURE                    Location/Qualifiers
source                     1..201
                           mol_type = genomic DNA
                           organism = Homo sapiens
SEQUENCE: 24
caagggggt ggagggagag cggggaagga ggggtgtca gctcaactgt aaaagctgca      60
cagatttttt ttcttttctct ctctctgcct tccatagat tgtttctgtt tcatgccctg   120
tctcatttcg catagctaaa aagaatgct aattaagatc ccttgtctta acctgaaaaa    180
taatgactcg gctgtaatta g                                             201

SEQ ID NO: 25              moltype = DNA   length = 201
FEATURE                    Location/Qualifiers
source                     1..201
                           mol_type = genomic DNA
                           organism = Homo sapiens
SEQUENCE: 25
gaggggaagc tggagcccca actttgatcc tccattggag tggcccaaat ctttccatct    60
agggcaagtc ctgaaaggcc caaggccccc tccccagtct ggccttggcc tccagcctgg   120
agaagggcta acatcagctc attgtcaagg ccaccccac cccagaacag aaccgtgtct    180
ctgataaagg ttttgaagtg a                                             201

SEQ ID NO: 26              moltype = DNA   length = 201
FEATURE                    Location/Qualifiers
source                     1..201
                           mol_type = genomic DNA
                           organism = Homo sapiens
SEQUENCE: 26
cgtcgctggg gccccatagt gtgcatcatg tccaacctgt aactctctcc ccctcttctt    60
ccatgaggtc ctgagaccag gattcctaaa acaaacagga tgagggacct ttagacacgc   120
aaggagacat gcctctagca ggatcagggg gactggggtc gggagggtgg ggcaggaagg   180
aagccagaat cagaagtatc c                                             201

SEQ ID NO: 27              moltype = DNA   length = 201
FEATURE                    Location/Qualifiers
source                     1..201
                           mol_type = genomic DNA
                           organism = Homo sapiens
SEQUENCE: 27
aagtttgaag agccattttg gtaaacggtt tttattaaag atgctatgga acataaagtt    60
gtattgcatg caatttgaag taacttattt gactatgaat attatcggat tactgaattg   120
tatcaatttg tttgtgttca atatcagctt tgataattgt gtaccttaag atattgaagg   180
agaaaataga taatttacaa g                                             201

SEQ ID NO: 28              moltype = DNA   length = 201
FEATURE                    Location/Qualifiers
source                     1..201
                           mol_type = genomic DNA
                           organism = Homo sapiens
SEQUENCE: 28
ccatgtcaac agtaataact aaagagtaac gttatgccat gtggtcatac tctcagcttg    60
ctgagtggat gacaaaaaga ggggaattgt taaaggaaaa tttaaatgga gactggaaaa   120
atcctgagca aacaaaacca cctgcccctt agaaatagct ttaactttgc ttaaactaca   180
aacacaagca aaacttcacg g                                             201

SEQ ID NO: 29              moltype = DNA   length = 201
FEATURE                    Location/Qualifiers
source                     1..201
                           mol_type = genomic DNA
                           organism = Homo sapiens
SEQUENCE: 29
```

```
aggcttggat gagaacagcg tgtagcctat gtttcctgtg cagtggtaat caccactgtg   60
actgtggttt gcttgtggga tggagaaggt gggatccaaa tgggagaatt tctgggattt  120
tccattctgg aagaatgtga ccttgaccag aggcttgtcc ttccagctgt ggcacctcag  180
catgatggtt tctccctcct g                                            201

SEQ ID NO: 30           moltype = DNA  length = 201
FEATURE                 Location/Qualifiers
source                  1..201
                        mol_type = genomic DNA
                        organism = Homo sapiens
SEQUENCE: 30
aggcgtgtgc cactacactc aactaatttt tgtatttta ggagagacgg ggtttcaccc   60
tgttggccag gctggtctcg aactcctgac ctcaagtgat tcacccacct tggcctcata  120
aacctgtttt gcagaactca tttattcagc aaatatttat tgagtgccta ccagatgcca  180
gtcaccacac aaggcactgg g                                            201

SEQ ID NO: 31           moltype = DNA  length = 201
FEATURE                 Location/Qualifiers
source                  1..201
                        mol_type = genomic DNA
                        organism = Homo sapiens
SEQUENCE: 31
tctaaatgta agagttcaga ctcacattct attaaatttt agccctaaaa tgacaagcct   60
tcttaaagcc ttatttttca aaagcgcccc ccccattctt gttcagatta agagttgcca  120
aaataccttc tgaactacac tgcattgttg tgccgagaac accgagcact gaactttgca  180
aagaccttcg tctttgagaa g                                            201

SEQ ID NO: 32           moltype = DNA  length = 201
FEATURE                 Location/Qualifiers
source                  1..201
                        mol_type = genomic DNA
                        organism = Homo sapiens
SEQUENCE: 32
gaaggaaact tggaaaagtt tgacaaatct gctctagagg gcctgtgcaa tttgaccatt   60
gaagaattcc gattagcata cttagactac tacctcgatg atattattga cttatttaat  120
tgtttgacaa atgtttcttc attttccctg gtgagtgtga ctattgaaag ggtaaaagac  180
ttttcttata atttcggatg g                                            201

SEQ ID NO: 33           moltype = DNA  length = 201
FEATURE                 Location/Qualifiers
source                  1..201
                        mol_type = genomic DNA
                        organism = Homo sapiens
SEQUENCE: 33
aaacctacgc gattaatcat cagtgtacag tttaggacta acaatccatt tattagtagc   60
agaaagaagt ttaaaatctt gctttctgat ataatttgtt ctgtaggccc caatatggga  120
ggtaaatcaa catatattcg acaaactggg gtgatagtac tcatggccca aattgggtgt  180
tttgtgccat gtgagtcagc a                                            201

SEQ ID NO: 34           moltype = DNA  length = 201
FEATURE                 Location/Qualifiers
source                  1..201
                        mol_type = genomic DNA
                        organism = Homo sapiens
SEQUENCE: 34
aaacctacgc gattaatcat cagtgtacag tttaggacta acaatccatt tattagtagc   60
agaaagaagt ttaaaatctt gctttctgat ataatttgtt ttgtaggccc caatatggga  120
ggtaaatcaa catatattcg acaaactggg gtgatagtac tcatggccca aattgggtgt  180
tttgtgccat gtgagtcagc a                                            201
```